(12) United States Patent
Gendron et al.

(10) Patent No.: US 6,696,415 B2
(45) Date of Patent: Feb. 24, 2004

(54) TREATMENT OF OCULAR NEOVASCULARIZATION AND RELATED DISEASES

(75) Inventors: Robert L. Gendron, Cincinnati, OH (US); Helene Paradis, Cincinnati, OH (US)

(73) Assignee: Children's Hospital Research Foundation, Cincinnati, OH (US)

( * ) Notice: Subject to any disclaimer, the term of this patent is extended or adjusted under 35 U.S.C. 154(b) by 0 days.

(21) Appl. No.: 09/836,503

(22) Filed: Apr. 17, 2001

(65) Prior Publication Data

US 2002/0137678 A1 Sep. 26, 2002

Related U.S. Application Data

(60) Provisional application No. 60/197,977, filed on Apr. 17, 2000.

(51) Int. Cl.[7] .......................... A61K 38/00; C12N 9/00; C07K 16/00
(52) U.S. Cl. ........................ 514/12; 435/183; 435/188.5
(58) Field of Search .............................. 435/183, 188.5; 514/12

(56) References Cited

PUBLICATIONS (Wess et al Washington Post 1998, May 6;6(20):A3).*
Kleinman, H.K., McGarvey, M.L., Liotta, L.A., Robey, P.G., Tryggvason, K., Martin, G.R. Isolation and characterization of type IV procollagen, laminin, and heparan sulfate proteoglycan from the EHS sarcoma. Biochemistry. 1982 21(24):6188–93.
Lou, D.A., Hu, F.N. Specific antigen and organelle expression of a long–term rhesus endothelial cell line. In Vitro Cell Dev. Biol., 1987, 23, 75–85.
Whiteway, M., Freedman, R., Van Arsdell, S., Szostak, J.W., and Thorner, J. (1987) The yeast ARD1 gene product is required for repression of cryptic mating–type information at the HML locus. Mol. Cell. Biol. 7, 3713–3722.
Lou, D.A., Hu, F.N. Co–distribution of von Willebrand factor and fibronectin in cultured rhesus endothelial cells. Histochem. J., 1987, 19, 431–438.
Mullen, J.R., Kayne, P.S., Moerschell, R.P., Tsunasawa, S., Gribskov, M. Colavito Shepanski, M. Grunstein, M., Sherman, F., and Sternglanz, R. (1989) Identification and characterization of genes and mutants for an N–terminal acetyltransferase from yeast. EMBO J. 8, 2067–2075.
Antonelli–Orlidge A, Saunders KB, Smith SR, D'Amore PA Proc Natl Acad Sci U S A 1989 Jun.;86(12):4544–8 An activated form of transforming growth factor beta is produced by cocultures of endothelial cells and pericytes.
Sivalingam, A., Kenney, J., Brown, G.C., Benson, W.E., Donoso, L. Basic fibroblast growth factor levels in the vitreous of patients with proliferative diabetic retinopathy. Arch Ophthalmol, 1990, 108(6):869–72.

Aparicio, O.M., Billington, B.L., and Gottschling, D.E. (1991) Modifiers of position effect are shared between telomeric and silent mating–type loci in S. cerevisiae. Cell 66, 1279–1287.
Vukicevic, S., Kleinman, H.K., Luyten, F.P., Roberts, A.B., Roche, N.S., Reddi, A.H. Identification of multiple active growth factors in basement membrane Matrigel suggests caution in interpretation of cellular activity related to extracellular matrix components. Exp Cell Res. 1992 202(1):1–8.
Park, E.C., and Szostak, J.W. (1992) ARD1 and NAT1 proteins form a complex that has N terminal acetyltransferase activity. EMBO J. 11, 2087–2093.
Kohner, E.M. Diabetic Retinopathy. BMJ, 1993, 307, 1195–1199.
Boeri, D., Cagliero, E., Podesta, F., Lorenzi, M. Vascular wall von Willebrand factor in human diabetic retinopathy. Invest Opthalmol. Vis. Sci., 1994, 35(2):600–7.
Aiello, L.P., Pierce, E.A., Foley, E.D., Takagi, H., Chen, H., Riddle, L., Ferrara, N., King, G.L., Smith, L.E.H. Suppression of retinal neovascularization in vivo by inhibition of vascular endothelial growth factor (VEGF) using sol–uble VEGF–receptor chimeric proteins. Proc Natl Acad Sci USA, 1995, 92, 10457–10461.
Robinson, G.S., Pierce, E.A., Rook, S.L., Foley, E., Webb, R., Smith, L.E.S. Oligodeoxynucleotides inhibit retinal neovascularization in a murine model of proliferative retinopathy. Proc Natl Acad Sci USA, 1996, 93:4851–4856.
Luna, J., Tobe, T., Mousa, S.A., Reilly, T.M., Campochiaro, P.A. Antagonists of integrin a–v b–3 inhibit retinal neovascularization in a murine model. Lab Invest, 1996, 75:563–573.
Hammes, H., Brownlee, M., Jonczyk, A., Sutter, A., Preissner, K. Subcutaneous injection of a cyclic peptide antagonist of vitronectin receptor–type integrins inhibits retinal neovascularization. Nat Med, 1996, 2:529–533.

(List continued on next page.)

*Primary Examiner*—Anthony C. Caputa
*Assistant Examiner*—Christopher Yaen

(57) ABSTRACT

Tubedown-1 (tbdn-1), a protein associated with acetyltransferase activity has been characterized and its cDNA isolated. Tbdn-1 regulates endothelial differentiation through protein acetylation, DNA-binding or by interacting with and/or acetylating other protein targets important for endothelial differentiation. In normal adult eyes, tbdn-1 is expressed highly in the corneal endothelium proper and in the vascular endothelium of the limbus and retina. Tbdn-1 is absent or downregulated in the vascular endothelia of diseased and injured eyes, including eyes from patients with proliferative retinopathies involving neovascularization. Inhibition of tbdn-1 expression in endothelial cells in vitro indicates tbdn-1 acts as an inhibitor of angiogenesis. Thus, high levels of tbdn-1 expression present in normal ocular endothelial cells is associated with suppression of abnormal neovascularization in the eye demonstrating the therapeutic usefulness of tbdn-1 as a regulator of retinal angiogenesis.

12 Claims, 8 Drawing Sheets

PUBLICATIONS

Gendron, R.L., Tsai, F.-Y., Paradis, H. and Arceci, R.J. Induction of Embryonic Vasculogenesis by bFGF and LIF in vitro and in vi *Dev. Biol.*, 1996, 177,332–347.

Mizutani, M., Kern, T.S., Lorenzi, M. Accelerated death of retinal microvascular cells in human and experimental diabetic retinopathy. J Clin Invest, 1996, 97(12):2883–90.

Frank, R.N., Amin, R.H., Eliott, D., Puklin, J.E., Abrams, G.W. Basic fibroblast growth factor and vascular endothelial growth factor are present in epiretinal and choroidal neovascular membranes. Am. J. Ophthalmol.,1996, 122, 393–403.

Ljubimov, A.V., Burgeson, R.E., Butkowski, R.J., Couchman, J.R., Zardi, L., Ninomiya, Y., Sado, Y., Huang, Z.S., Nesburn, A.B., Kenney, M.C. Basement membrane abnomalities in human eyes with diabetic retinopathy. J Histochem Cytochem 1996 44(12):1469–79.

Paques, M., Massin, P., Gaudric, A. Growth factors and diabetic retinopathy. Diabetes Metab, 1997, 23(2):125–30.

Miller, J.W. Vascular endothelial growth factor and ocular neovascularization. Am. J. Pathol., 1997, 151, 13–23.

Amin, R.H., Frank, R.N., Kennedy, A., Eliott, D., Puklin, J.E., Abrams, G.W. Vascular endothelial growth factor is present in glial cells of the retina and optic nerve of human subjects with nonproliferative diabetic retinopathy. Invest. Ophthalmol. Vis. Sci., 1997, 38, 36–47.

Lutty, G.A., Cao, J., McLeod, D.S. Relationship of polymorphoniclear leukocytes to capillary dropout in the human diabetic choroid. Am J Pathol, 1997, 151(3):707–14.

Boulton, M., Gregor, Z., McLeod, D., Charteris, D., Jarvis–Evans, J., Moriarty, P., Khaliq, A., Foreman, D., Allamby, D., Bardsley, B. Intraviteral growth factors in proliferative diabetic retinopathy: correlation with neovascular activity and glycaemic management. Br J Ophthalmol, 1997, 81(3):228–33.

Good, W.V., Paradis, H., Adams, L.C. and Gendron, R.L. Ocular spatial distribution of tubedown–1 (tbdn–1), a novel acetyltransferase regulated in endothelial cell differentiation. The Association for Research in Vision and Ophthalmology (ARVO) Annual Meeting May 9–14, 1998, Fort Lauderdale, Florida.

Invited participant in *Electronic Workshop on Genetic Manipulation in Animals: Advanced Transgenesis and Cloning*. National Institute of Standards and Technology, U.S. Department of Commerce, Advanced Technology Program Website: http://www.atp.nist.gov/atc/atc–6.htm. Sep., 1998. *Prospects and hurdles in optimizing the vascular support of engineered tissues.*

Infeld, D.A., O'Shea, J.G. Diabetic retinopathy. Postgrad. Med. J., 1998, 74, 129–133.

Robinson, G.S., Aiello, L.P. Angiogenic factors in diabetic ocular disease: mechanisms of today, therapies for tomorrow. Int. Ophthalmol. Clin., 1998, 38, 89–102.

Hammes, H.P., Lin, J., Bretze, R.G., Brownlee, M., Breier, G. Upregulation of the vascular endothelial growth factor/vascular endothelial growth factor receptor system in experimental background diabetic retinopathy of the rat. Diabetes, 1998, 47, 401–406.

Gendron, R.L., Adams, L.C. and Paradis, H. Tubedown–1, a novel Acetyltransferase associated with vascular remodeling. Experimental Biology '99. Washington, DC, Apr. 1999.

Kon, C.H., Occleston, N.L., Aylward, G.W., Khaw, P.T. Expression of vitreous cytokines in proliferative vitreoretinopathy: a prospective study. Invest Ophthalmol Vis Sci, 1999, 40(3):705–12.

Ozaki, H., Seo, M.S., Ozaki, K., Yamada, H., Yamada, E., Okamoto, N., Hofmann, F., Wood, J.M., Campochiaro, P.A. Blockade of vascular endothelial cell growth factor receptor signaling is sufficient to completely prevent retinal neovascularization. Am J Pathol., 2000, 156(2):697–707.

Gendron, R.L., Adams, L.C., and Paradis, H. *Tubedown–1*, a novel acetyltranferase Associated with Blood Vessel Developme *Develp[Dyn.*, 2000, In press.

Paradis, H., and Gendron, R.L. LIF transduces contradictory signals on capillary outgrowth through induction of Stat3 and $p^{41/43}$ MAP kinase. *J. Cell Science*, 2000, 113, 4331–4339.

Demaine, A., Cross, D., Millward, A. Polymophisms of the aldose reductase gene and susceptibility to retinopathy in type 1 diabetes mellitus. Invest Opthalmol Vis Sci., 2000 41(13):4064–4068.

Podesta, F., Romeo, G., Liu, W.H., Krajewski, S., Reed, J.C., Gerhardinger, C., Lorenzi, M. Bax is increased in the retina of diabetic subjects and is associated with pericyte apoptpsis in vivo and in vitro. Am J Pathol. 2000, 156(3):1025–1032.

* cited by examiner

TREATMENT OF OCULAR NEOVASCULARIZATION AND RELATED DISEASES

This application is based on and claims priority from U.S. Provisional Patent Application Ser. No. 60/197,977, Robert L. Gendron, filed Apr. 17, 2000.

FEDERAL SUPPORT STATEMENT

This work was supported in part by NIH Grant No. R01 EY12827

FIELD OF INVENTION

This invention is directed to angiogenesis inhibitor compounds and methods of using these compositions to prevent and/or treat neovascularization in human patients. In particular, the compositions are useful for controlling ocular neovascularization through exogenous and endogenous therapeutic routes.

BACKGROUND

Angiogenesis is the formation of new capillary blood vessels leading to neovascularization (1). Angiogenesis is a complex process which includes a series of sequential steps including endothelial cell-mediated degradation of vascular basement membrane and interstitial matrices, migration of endothelial cells, proliferation of endothelial cells, and formation of capillary loops by endothelial cells. Though angiogenesis is a normal process for the development or maintenance of the vasculature, pathological conditions (i.e., angiogenesis dependent diseases) arise where blood vessel growth is actually harmful. Such pathologies include psoriasis, arthritis and tumor development. The progression of angiogenesis occurs in several phases which include: elaboration of the angiogenic signal; dissolution of the blood vessel basement membrane; endothelial cell proliferation; endothelial cell migration; and formation and differentiation of capillary tubules and loops. Each of these phases is a potential target for pharmacological intervention. Antiangiogenic therapy would allow modulation in such angiogenesis-associated diseases having excessive vascularization.

Angiogenesis is also associated with other important diseases of ocular tissue, including diabetic retinopathies, proliferative vitreoretinopathies and retinopathy of prematurity. Any abnormal growth of blood vessels in the eye can scatter and block the incident light prior to reaching the retina. Neovascularization can occur at almost any site in the eye and significantly alter ocular tissue function. Some of the most threatening ocular neovascular diseases are those which involve the retina. For example, many diabetic patients develop a retinopathy which is characterized by the formation of leaky, new blood vessels on the anterior surface of the retina and in the vitreous causing proliferative vitreoretinopathy. A subset of patients with age related macular degeneration develop subretinal neovascularization which leads to their eventual blindness.

The fundamental process of the formation and growth of endothelial vessels occurs during fetal development, the female endometrial cycle, wound healing, inflammation, tumor progression and tissue grafting (2, 3). In the eye, the neovascularization (de novo proliferation of endothelium and blood vessels) of ocular structures during disease or injury can disrupt ocular physiological balance and can lead to vision loss and/or blindness. Although arising from a different embryonic origin (4, 5), corneal endothelium also can undergo abnormal transdifferentiation and cause disruption of vision and blindness. Examples of visual disruption caused by ocular endothelial disfunction, proliferation and neovascularization include the retinopathies resulting as a complication from gestational prematurity, diabetes or age related macular degeneration and the iridocorneal endothelial syndromes (ICE) affecting the cornea and iris. Thus, ocular endothelia must be equipped with innate mechanisms for inhibiting excess endothelial proliferation, angiogenesis and transdifferentiation in highly specialized but relatively "avascular" regions such as the retina and cornea.

Several diseases involving proliferative neovascularization affect the retina and can cause visual disruption and/or blindness. The normal gradual development of a retinal blood vessel network is interrupted in retinopathy of prematurity (ROP), which results from an abnormal proliferation or neovascularization of retinal blood vessels in pregestational infants. In primary hyperplastic vitreous (PHPV), the vitreal vasculature which normally regresses late in gestation fails to regress. In ROP, retinal blood vessels which normally grow into the retinal layers in a temporally balanced manner, over-proliferate in dense patches which can lead to a range of retinal abnormalities. These defects include scarring, retinal detachment and later vision loss in those cases which do not show spontaneous regression (6–17). Abnormal vitreal vessels, which form a network between the retina and the lens, may contain subendothelial pericytes which can contract and detach the retina. To date, the only effective treatment for ROP involves ablation of the peripheral retina in an attempt to physically limit the vascular overgrowth causing the sequelae leading to later vision loss and blindness. This treatment can help to prevent blindness in ROP patients. However, retinal ablation for the ROP disease itself leaves most ROP patients with visual acuity of less than 20/40 (18).

Ocular pathology associated with diabetes mellitus ranges from retinopathy (DRO) and neovascularization of the iris to glaucoma as an end-stage complication of anterior chamber disfunction. DRO results from a twofold complication of initial retinal vascular thrombotic occlusion followed by proliferative retinal neovascularization as a result of the hypoxia caused by the vascular occlusion. The pathophysiological consequences of DRO include macular edema, ischemia and degeneration, retinal detachment, vitreous hemorrhage and optic nerve abnormalities (28). The only effective treatment for DRO is ablative therapy using lasers to photocoagulate the proliferate areas of neovascularization. However, laser therapy involves complications including retinal vein occlusion, loss of visual acuity, vitreous hemorrhage and sometimes fails altogether (20). A range of angiogenic factors and other cytokines likely contribute to neovascularization in DRO (21, 22, 23). The high serum glucose level characteristic of diabetes may itself contribute to retinal neovascularization in diabetic patients as high glucose has been shown to elevate VEGF (vascular endothelial growth factor) production from vascular smooth muscle cells (24). Both VEGF and the VEGF-R1 and VEGF-R2 are upregulated in vascular and perivascular regions of the retina in diabetic rats (25). In DRO specimens examined at stages before proliferative neovascularization peaks, VEGF is found to be expressed in retinal glial cells, retinal pigment epithelial cells and even in retinal vascular endothelial cells (26). This early production of VEGF may contribute to the later proliferative neovascularization that leads to pathological sequalae in later stages of DRO. DRO is associated with a highly abnormal local retinal microenvironment which promotes retinal neovascularization.

Macular degeneration (MDG) is the leading cause of blindness in people over age 60. The formation of a choroidal fibrovascular membrane in retinas of macular degeneration patients contributes to retinopathy and retinal detachment. Inflammatory cytokines and angiogenic growth factors including platelet derived growth factor (PDGF), acidic fibroblast growth factor (aFGF), bFGF, TGF-b1, and VEGF have been found to be present in both the retinal pigment epithelium and in the fibrovascular membranes associated with macular degeneration (26, 27). High levels of VEGF and other angiogenic cytokines are thought to lead to increased neovascularization which contributes to a positive feedback cycle of fibrovascular growth, retinal dysplasia, scarring and eventual retinal detachment.

Retinal neovascularization is often treated with multiple laser burns to the retina to remove the pathological vasculature. Patients with neovascular diseases of the anterior chamber (e.g. corneal neovascularization, iritis rubeosis) are treated with potent topical ocular glucocorticoids. These therapies are only partially effective and generally only slow neovascularization and the progress of the overall disease. In addition, they can cause severe side effects if used over a relatively long period of time.

Other attempts have been made to provide therapies for the prevention or treatment of pathological angiogenesis. For example, angiostatic steroids functioning to inhibit angiogenesis in the presence of heparin or specific heparin fragments have been described (28). Another group of angiostatic steroids useful in inhibiting angiogenesis is disclosed in commonly assigned U.S. Pat. No. 5,371,078, Clark et al., which is herein incorporated by reference.

Glucocorticoids have also been shown to inhibit angiogenesis. However, the use of glucocorticoid therapy in general is complicated by the inherent problems associated with steroid applications. Such problems include elevated intraocular pressure (29). Still other therapies have included the use of protamine (30), the use of calcitriol (31), and the use of the antibiotic, fumagillin and its analogs, disclosed in EP 354787.

Identification and characterization of new molecules regulating the formation and growth of retinal endothelium is a necessary objective for designing new therapies for controlling diseases involving retinal neovascularization. The inventors have cloned a new gene named tubedown-1 (tbdn-1), which encodes a novel protein associated with an acetyltransferase activity (32). Expression of tbdn-1 is high in developing vascular structures, including the developing vitreal vasculature, and is downregulated as tissues mature. Postnatally, tbdn-1 expression remains high in corneal, limbic, choroidal and retinal endothelia of the normal eye. Tbdn-1 is downregulated during capillary angiogenesis of IEM embryonic endothelial cells and RF/6A choroid-retina endothelial cells in vitro.

Agents which inhibit neovascularization are known by a variety of terms such as angiostatic, angiolytic, angiogenesis inhibitors or angiotropic agents.

SUMMARY OF THE INVENTION

A novel and highly conserved protein associated with an acetyltransferase activity named tubedown-1 (tbdn-1) has been isolated and characterized. Tbdn-1 regulates endothelial differentiation through protein acetylation, DNA-binding or by interacting with and/or acetylating other protein targets important for endothelial differentiation. Tbdn-1 is expressed during maturation of the developing vitreal vasculature. In normal adult eyes, tbdn-1 is expressed in the corneal endothelium proper and in the vascular endothelium of the limbus and retina. Tbdn-1 is absent or downregulated in the vascular endothelia of diseased and injured eyes, including eyes from patients with proliferative retinopathies involving neovascularization such as diabetic retinopathy, age related macular degeneration and retinopathy of prematurity. Tbdn-1 is downregulated during capillary differentiation of both IEM endothelial cells and RF/6A choroid-retina endothelial cells in vitro. Inhibition of tbdn-1 expression in IEM and RF/6A endothelial cells in vitro indicates tbdn-1 acts as an inhibitor of angiogenesis. These results taken together indicate that high levels of tbdn-1 expression present in normal ocular endothelial cells is associated with suppressing ocular neovascularization.

Accordingly, the gene tbdn-1, the cDNA of tbdn-1 (SEQ ID NO. 1), an open reading frame of tbdn-1 (such as SEQ ID NO. 6), and nucleotide sequences showing at least 70% sequence homology to SEQ ID NO. 1 or SEQ ID NO. 6, amino acid sequences translated from the cDNA of SEQ ID NO. 1, such as SEQ ID NOS. 2, 3, 4, and 5, and others amino acid sequences showing at least 85% sequence homology to SEQ ID NOS. 2, 3, 4, and 5 and which also exhibit anti-angiogenic activity may all be used as anti-angiogenic agents for treatment of ocular neovascularization. Compositions comprising a pharmaceutically effective amount of an amino acid sequence, which shows anti-angiogenic activity, that is translated from cDNA of SEQ ID NO. 1, particularly the amino acid sequences selected from the group consisting of SEQ ID NOS. 2, 3, 4 5 and a pharmaceutically acceptable carrier are also within the scope of this invention.

Methods for treating, inhibiting or delaying the onset of angiogenesis-associated diseases in mammals, wherein the angiogenesis-associated diseases are related to ocular neovascularization, are also within the scope of this invention. This method of treatment comprises treating the mammal with a pharmaceutically effective amount of an exogenously produced amino acid sequence showing anti-angiogenic activity and which is translated from the cDNA of SEQ ID NO. 1. These amino acid sequences include, but are not limited to sequences given in SEQ ID NOS. 2, 3, 4 and 5. The angiogenesis-associated diseases include, but are not limited to diabetic retinopathy, retinopathy of prematurity, primary hyperplastic vitreous, macular degeneration and any other conditions involving ocular neovascularization. The amino acid sequence may be contained in a pharmaceutically acceptable carrier and administered by intraocular injection, subretinal injection, subscleral injection, intrachoroidal injection, subconj unctival injection, topical administration or oral administration.

A gene therapy approach for treatment of mammals afflicted with an angiogeneis-associated disease, such as those related to ocular neovascularization, and in particular diabetic retinopathy and retinopathy of prematurity is also provided. For this method of treatment, an amino acid sequence, having anti-angiogenic activity, is translated from the cDNA of SEQ ID NO.1, and is provided to cells of a mammal having a deficiency in that amino acid sequence. This method further comprises administering into the cells a vector comprising and expressing a DNA sequence encoding the desired amino acid sequence, and expressing the DNA sequence in the cells to produce amino acid sequence. Cells harboring the vector secrete the amino acid sequence and this sequence is subsequently taken up by other cells deficient in the amino acid sequence. The amino acid sequences include, but are not limited to SEQ ID NO. 2, SEQ ID NO. 3, SEQ ID NO. 4 and SEQ ID NO. 5.

A, Tbdn-1 staining in the hyaloid (h) and tunica vasculosa lentis (tvl) vessels of the developing human eye at approximately 10 weeks of gestation (arrows indicate the hyaloid and or the tunica vasculosa lentis capillary networks). B, a section adjacent to (A) stained with preimmune IgY, which is a negative control for the anti-tbdn-1 antibody staining. C, a section adjacent to (A & B) stained with anti-Von Willibrand Factor antibody, which stains and labels endothelial cells (arrows indicate VWF positive endothelial cells). D, a section adjacent to those above stained with anti-alpha smooth muscle actin antibody, which stains and labels the contractile pericyte like cells interspersed in these capillary networks (arrows indicate ASMA positive pericyte like cells). le, lens; arrows in all panels indicate hyaloid and or tunica vasculosa lentis blood vessels; scale bars equal 50 um.

Figure 4:
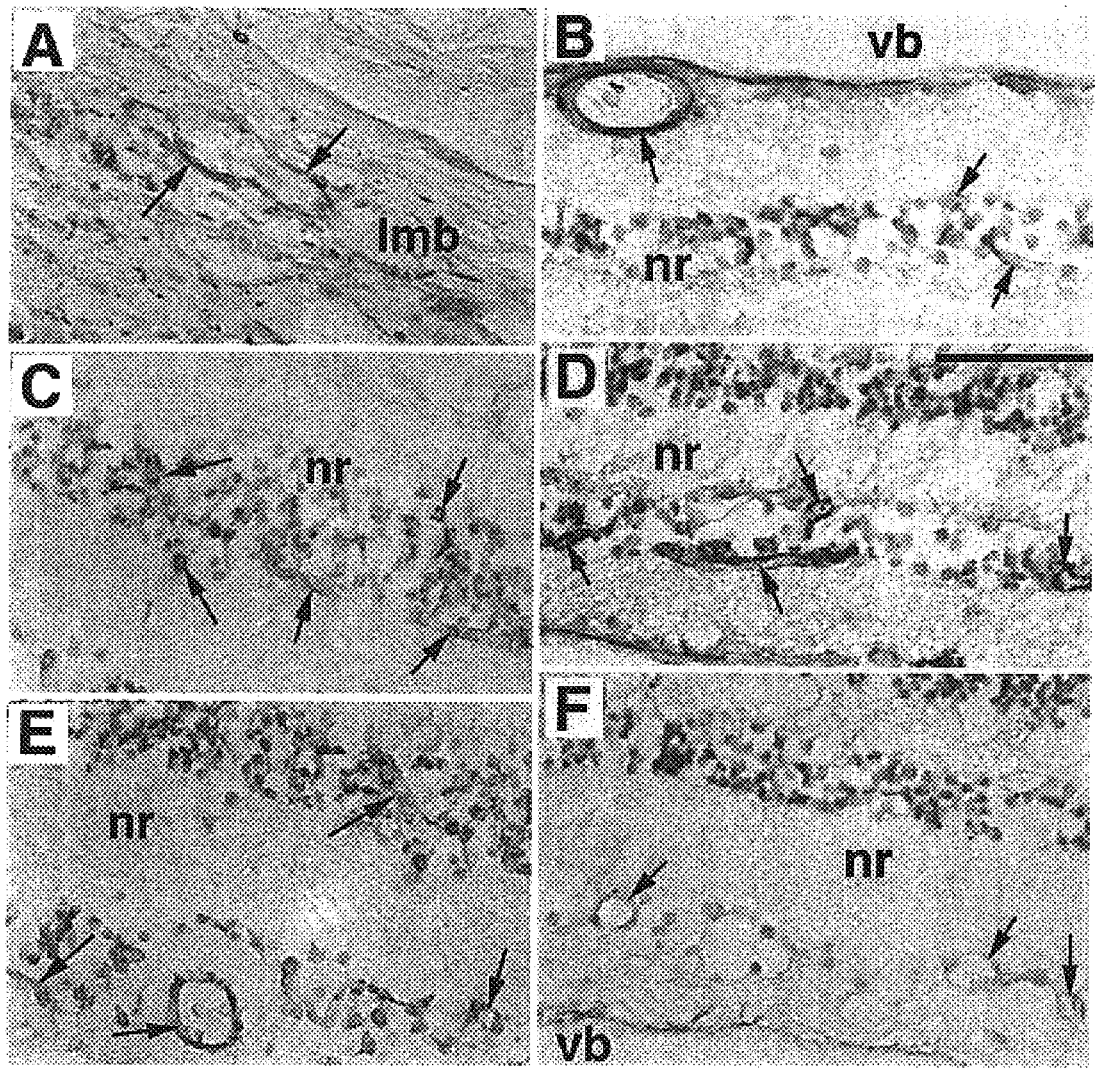

FIG. 4. Tbdn-1 protein and endothelial marker expression in sections of normal adult human eye. A, Limbic vessel tbdn-1 expression (red stain, arrows, indicate tbdn-1 positive endothelial cells in a limbic blood vessel). C, E, Retinal endothelial tbdn-1 expression in longitudinally and transverse sectioned blood vessels in normal adult eye (red stain, arrows, indicate tbdn-1 positive endothelial cells in retinal blood vessels). B, D, Retinal endothelial Von Willibrand factor expression in longitudinally and transverse sectioned blood vessels in normal adult eye (red stain, arrows, indicate Von Willibrand factor positive endothelial cells in retinal blood vessels). Adjacent sections stained with equal concentrations of preimmune IgY control antibody showed no staining (F). Sections were developed using alkaline phosphatase and fast red substrate; Methyl green counterstain; lmb, limbic region of cornea; nr, neural retina; vb, vitreous body; scale bar in D indicates 50 um for all panels.

Figure 5:
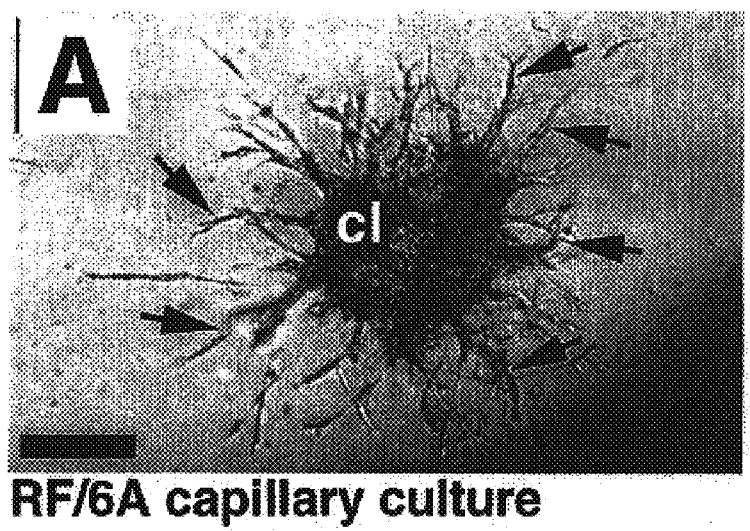
Figure 5:
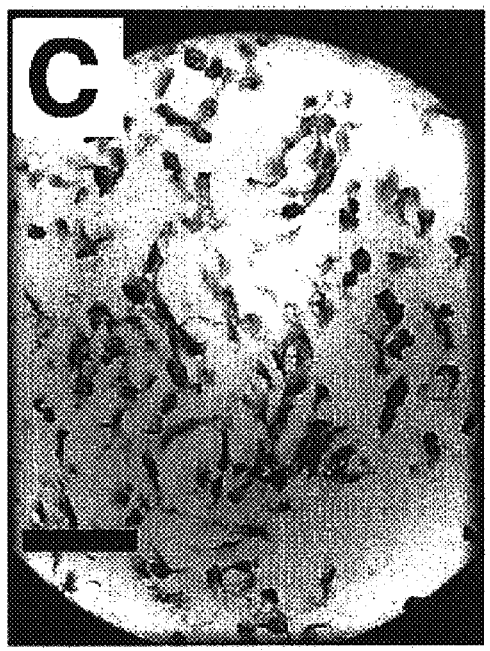
Figure 5:
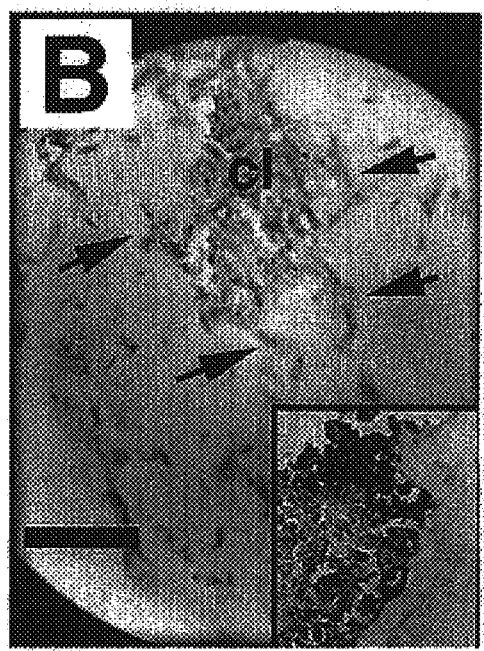

FIG. 5. Suppression of tbdn-1 protein expression in RF/6A cells in vitro during induction of capillary formation on Matrigel. C, Sections of RF/6A cells harvested from untreated cultures which were fixed and paraffin embedded were highly positive when stained using anti-tbdn-1 Ab1272 (dark red stain). A, RF/6A capillary colonies shown in culture before processing. B, After fixation, embedding, sectioning and staining with anti-tbdn-1 Ab1272, RF/6A capillary colonies showed low staining levels for tbdn-1 (arrows in B indicate similar capillary sprouts as arrowed in A, while cl indicates main body of colony). Sections of RF/6A capillary colonies from the same preparation stained very strongly with anti-tubulin positive control antibody (inset in B, dark red stain). Sections of RF/6A cells and capillary colonies stained with equal concentrations of pre-immune IgY were negative (not shown). Staining of sections was developed using alkaline phosphatase and fast red substrate; Scale bar equals 50 um; methyl green counterstain in (B) reveals the capillary sprouts (arrowed in the capillary colony before processing in A and also arrowed after processing in B) sprouting from the RF/6A colonies (cl).

Figure 6:
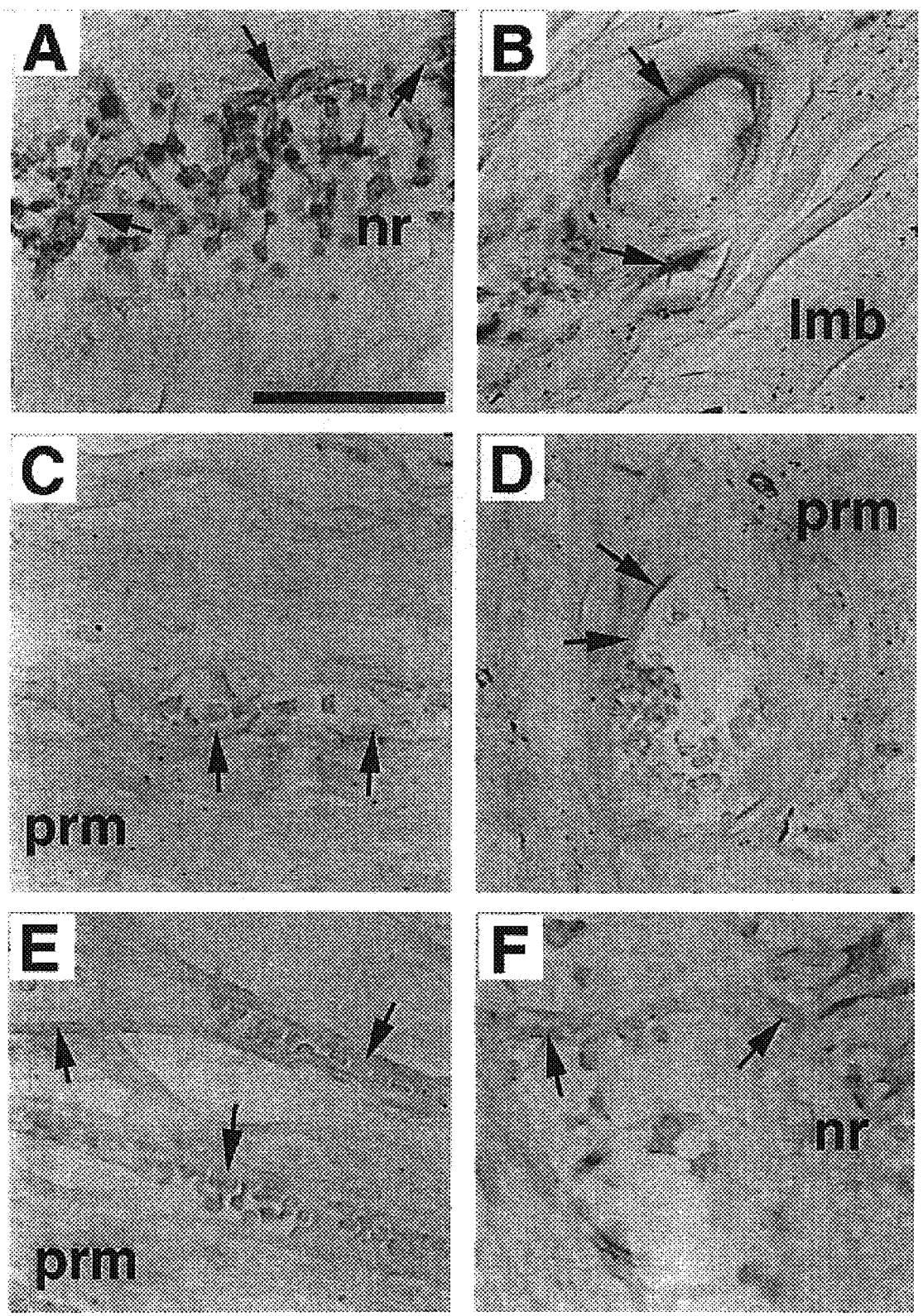

FIG. 6. Tbdn-1 protein expression is suppressed in specimens of eyes from patients with proliferative diabetic retinopathy (PDR). A, Retinal endothelial tbdn-1 expression (arrows indicate retinal blood vessels which are stained red) in normal adult eye. C–E, Tbdn-1 staining in blood vessels in preretinal membranes in sections of eyes from 3 separate representative PDR patients. F, Tbdn-1 staining in blood vessel fronds cut longitudinally in a neural retinal area in a section of eye from a fourth and separate representative PDR patient. Insets in both panels C and F show Von Willibrand Factor staining of abnormal blood vessels (arrows) in sections from the same PDR specimens and adjacent to those stained for tbdn-1. Blood vessels in the diseased retinal tissue show either very low levels of tbdn-1 expression or no detectable tbdn-1 expression compared to normal specimens while the same abnormal blood vessels express Von Willibrand Factor. B, shows tbdn-1 staining (arrowed, red) of limbic blood vessels in the anterior part of the same section as that shown in D to exemplify normal tbdn-1 expression in unaffected areas of eyes from patients with PDR. All sections were also incubated with equal concentrations of preimmune IgY and showed no staining (see example in FIG. 2). Sections were developed using alkaline phosphatase and fast red substrate; Methyl green counterstain; Scale bar equals 50 um for all panels; nr, neural retina; 1mb, limbic region of cornea; prm, preretinal membrane.

Figure 7:
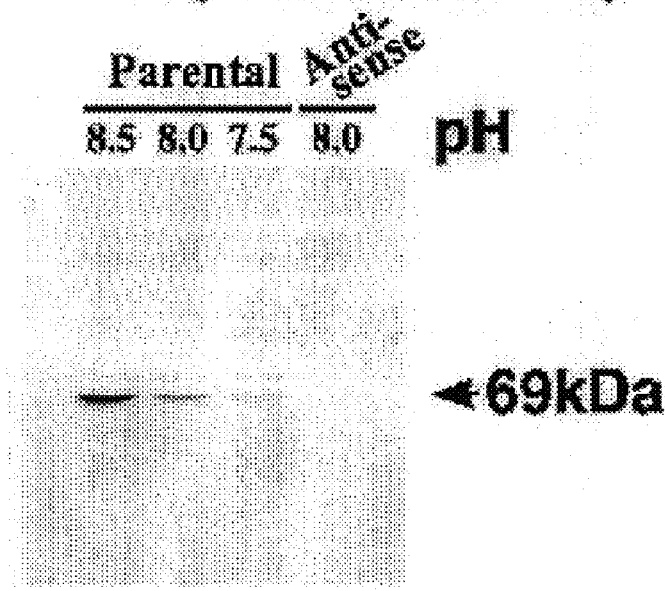

FIG. 7. IPs prepared from RF/6A cells showing inhibition of tbdn-1 protein expression display decreased acetyltransferase activity Acetyltransferase acitivity analysis of tbdn-1 immunoprecipitates prepared from whole cell lystates of the untrasfected rhesus RF/6A choroid-retina endothelial cell line (RF/6A Parental), and in 3 separate clones of RF/6A cells stably expressing a tbdn-1 antisense cDNA fragment (RF/6A-AStbdn-1), as indicated. The acetylated 69 kDa band, representing autoacetylation of tbdn-1, is indicated by the arrow.

Figure 8:
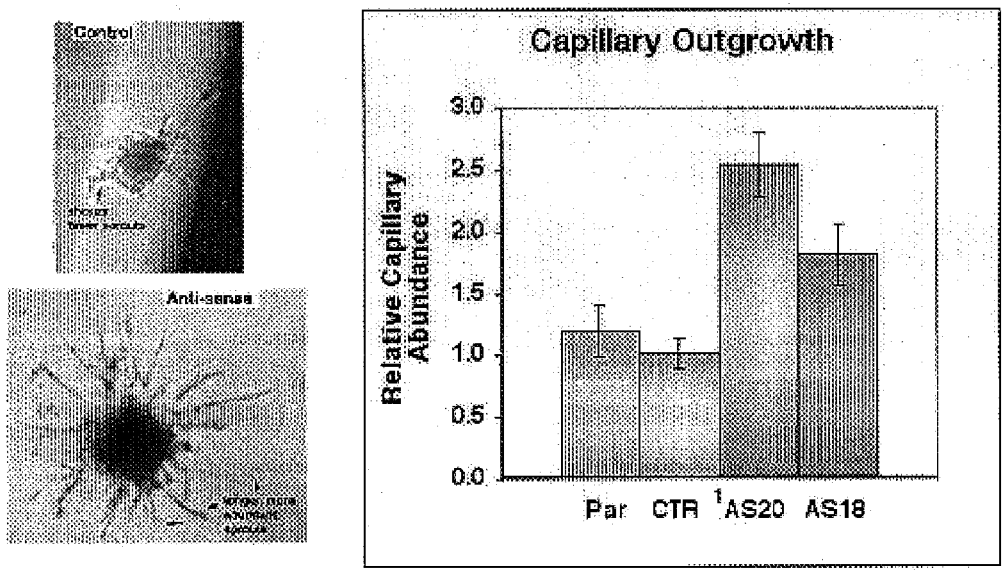

FIG. 8. Inhibition of tbdn-1 expression augments capillary formation of RF/6A endothelial cells in a Matrigel capillary formation assay. Left panel: Capillary colonies of RF/6A cells overexpressing antisense tbdn-1 cDNA (AS-tbdn-1) show a significantly augmented capillary outgrowth response compared to RF/6A cell clones expressing vector control (Control). Right panel: Capillary colonies formed by both IEM and RF/6A AS-tbdn-1 cDNA transfectant clones show longer, more complex and more abundant capillary sprouts than vector controls, as indicated by the histograms.

DETAILED DESCRIPTION OF THE INVENTION

Definitions

The terms "amino acid" or "amino acid sequence," as used herein, refer to an oligopeptide, peptide, polypeptide, or protein sequence, or a fragment of any of these, and to naturally occurring or synthetic molecules. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

The term "anti-angiogenic activity" as used herein, refers to the inhibition and/or moderation of angiogenesis.

The term "angiogenesis-associated disease" is used herein, for purposes of the specification and claims, to mean certain pathological processes in humans where angiogenesis is abnormally prolonged. Such angiogenesis-associated diseases include diabetic retinopathy, chronic inflammatory diseases, rheumatoid arthritis, dermatitis, psoriasis, stomach ulcers, and most types of human solid tumors.

The term "angiogenesis inhibitor" is used herein, to mean a biomolecule including, but not limited to, peptides, proteins, enzymes, polysaccharides, oligonucleotides, DNA, RNA, recombinant vectors, and drugs which function to inhibit angiogenesis. Angiogenesis inhibitors are known in the art and include natural and synthetic biomolecules.

The term "anti-angiogenic therapy" is used herein, for purposes of the specification and claims, to mean therapy targeted to vasculature expressing endoglin (expressed at higher levels on proliferating vasculature as compared to quiescent vasculature); whether the therapy is directed against angiogenesis (i.e., the formation of new capillary blood vessels leading to neovascularization), and/or existing vasculature and relating to a disease condition (e.g., vascular targeting therapy).

As used herein, the term "biologically active" refers to a protein having structural, regulatory, or biochemical functions of a naturally occurring molecule.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological function of the natural molecule. A derivative polypeptide is one modified, for instance by glycosylation, or any other process which retains at least one biological function of the polypeptide from which it was derived.

As used herein, the term "gene" or "recombinant gene" refers to a nucleic acid comprising an open reading frame encoding tbdn-1, including both exon and (optionally) intron sequences. A "recombinant gene" refers to nucleic acid encoding tbdn-1 and comprising tbdn-1-encoding exon sequences, though it may optionally include intron sequences which are either derived from a chromosomal tbdn-1 gene or from an unrelated chromosomal gene. An exemplary tbdn-1 recombinant gene is represented by SEQ ID No: 1. The term "intron" refers to a DNA sequence present in a given tbdn-1 gene which is not translated into protein and is generally found between exons.

The words "insertion" or "addition," as used herein, refer to changes in an amino acid or nucleotide sequence resulting in the addition of one or more amino acid residues or nucleotides, respectively, to the sequence found in the naturally occurring molecule.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single-stranded (such as sense or antisense) and double-stranded polynucleotides.

The phrases "percent identity" or "percent homology" refers to the percentage of sequence similarity found in homologues of a particular amino acid or nucleic acid sequence when comparing two or more of the amino acid or nucleic acid sequences.

As used herein, the term "transfection" means the introduction of a nucleic acid, e.g., an expression vector, into a recipient cell by nucleic acid-mediated gene transfer.

"Transformation", as used herein, refers to a process in which a cell's genotype is changed as a result of the cellular uptake of exogenous DNA or RNA, and, for example, the transformed cell expresses a recombinant form of tbdn-1, or where anti-sense expression occurs, from the transferred gene, the expression of a naturally-occurring form of tbdn-1 is disrupted.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. Vectors may also be viral vectors wherein the viral vector is selected from the group consisting of a lentivirus, adenovirus, adeno-associated virus and virus-like vectors. The vector may also be a lipid vesicle. The invention is intended to include such other forms of expression vectors which serve equivalent functions and which become known in the art subsequently hereto.

Discussion

Tbdn-1 encodes a novel 69 kDa protein associated with acetyltransferase activity (32). Tbdn-1 is downregulated during IEM and RF/6A capillary formation in vitro. Inhibition of tbdn-1 by expression of antisense tbdn-1 cDNA augments capillary formation of IEM and RF/6A cells. These results support a hypothesis that tbdn-1 plays a role in dampening and/or moderating physiological angiogenesis. Thus, the therapeutic modulation of tbdn-1 may be useful for treating ocular neovascularization.

Tbdn-1 expression peaks during early to middle stages of development of most blood vessels and is downregulated at later stages of maturation, suggesting it may be involved with regulating specific stages of blood vessel maturation during embryogenesis (32). This is exemplified by tbdn-1 expression in yolk vasculature development, in which tbdn-1 is expressed most highly during early stages of yolk sac vasculature formation, and is downregulated at the later stages of development during which time angiogenesis of the vitelline vasculature occurs (32). Tbdn-1 is not detected in most adult vascular beds, but persists at high levels in the adult ocular vasculature. High levels of expression of tbdn-1 are associated with ocular endothelial homeostasis in adult. Conversely, low levels of tbdn-1 expression are associated with endothelial capillary outgrowth in vitro and retinal neovascularization in vivo. Since the expressed tbdn-1 protein is a member of a family of regulatory enzymes, which are known to control a range of processes including cell growth and differentiation through posttranslational modification, tbdn-1 is hypothesized to be involved in maintaining homeostasis and preventing retinal neovascularization.

In normal adult eyes, tbdn-1 is highly expressed in the corneal endothelium proper and in the vascular endothelium of the limbus and retina. Tbdn-1 is absent or downregulated in the vascular endothelia of diseased and injured eyes including eyes from patients with proliferative retinopathies involving neovascularization. Thus, high levels of tbdn-1 expression present in normal ocular endothelial cells is associated with suppressing neovascularization in the eye. Accordingly, the gene tbdn-1, its analogues, the proteins which tbdn-1 encodes for and its analogues as well as the cDNA sequence, may be used therapeutically to regulate retinal angiogenesis.

Methods of Treatment

In accordance with the method of the present invention, an effective amount of the cDNA of tbdn-1 as isolated in a purified form (SEQ ID NO. 1), modified versions thereof showing at least 70% sequence homology, the protein the cDNA encodes for (SEQ ID. NO. 2), or modified versions of that protein, including but not limited to SEQ ID NOS. 3, 4 and 5, modified versions thereof showing at least 85% sequence homology, or modifications of accessory components of the signaling pathway in which tbdn-1 is active, or combinations thereof, may be used as an anti-angiogenic agents for the treatment of ocular neovascularization and related diseases. Additionally, the open reading frame sequence of the cDNA of tbdn-1 (base pairs 408–2186, SEQ ID NO. 6) coding for the expressed tbdn-1 protein (SEQ ID NO. 2) may also be used as an anti-angiogenic agent. All of these substances will be collectively referred to as "tbdn-1 agents."

The tbdn-1 derived angiogenesis inhibitor agents of the present invention are useful in inhibiting pathological neovascularization in mammals. As used herein, the term "pathological neovascularization" refers to those conditions where the formation of blood vessels (neovascularization) is harmful to the patient. Examples of pathological neovascularization dependent diseases include: head trauma, spinal trauma, systemic or traumatic shock, stroke, hemorrhagic shock, cancer, arthritis, arteriosclerosis, angiofibroma, arteriovenous malformations, corneal graft neovascularization, delayed wound healing, diabetic retinopathy, granulations, burns, hemangioma, hemophilic joints, hypertrophic scars, ocular neovascularization, nonunion fractures, Osler-Weber Syndrome, psoriasis, pyogenic granuloma, retrolental fibroplasia, pterigium, scleroderma, trachoma, vascular adhesions, and solid tumor growth.

In particular, the compositions are useful in preventing and treating any ocular neovascularization, including, but not limited to: retinal diseases (diabetic retinopathy, chronic glaucoma, retinal detachment, sickle cell retinopathy and subretinal neovascularization due to senile macular degeneration); rubeosis iritis; proliferative vitreoretinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury.

The tbdn-1 agents can be used therapeutically either as exogenous materials or as an endogenous materials. Exogenous tbdn-1 agents, are those produced or manufactured outside of the body and administered to the body. Endogenous tbdn-1 agents are those produced or manufactured inside the body by some type of device (biologic or other) for delivery to within or to other organs in the body. Tbdn-1 is present in body tissue. Patients who suffer from ocular neovascularization have a tendency to have decreased levels of expressed tbdn-1 in the ocular endothelial cells.

Endogenous Therapy

The principles of gene therapy for the production of therapeutic products within the body include the use of delivery vehicles (termed vectors) that can be non-pathogenic viral variants, lipid vesicles (liposomes), carbohydrate and/or other chemical conjugates of nucleotide sequences encoding the therapeutic protein or substance. These vectors are introduced into the body's cells by physical (direct injection), chemical or cellular receptor mediated uptake. Once within the cells, the nucleotide sequences can be made to produce the therapeutic substance within the cellular (episomal) or nuclear (nucleus) environments. Episomes usually produce the desired product for limited periods whereas nuclear incorporated nucleotide sequences can produce the therapeutic product for extended periods including permanently.

In clinical settings, the gene delivery systems for therapeutic tbdn-1 genes can be introduced into a patient (or non-human animal) by any of a number of methods, each of which is known in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

Gene therapy methodologies can also be described by delivery site. Fundamental ways to deliver genes include ex vivo gene transfer, in vivo gene transfer and in vitro gene transfer. In ex vivo gene transfer, cells are taken from the patient and grown in cell culture. The DNA is transfected into the cells, and the transfected cells are expanded in number and then reimplanted in the patient. In in vitro gene transfer, the transformed cells are cells growing in culture, such as tissue culture cells, and not particular cells from a particular patient. These "laboratory cells" are transfected, and the transfected cells are selected and expanded for either implantation into a patient or for other uses. In vivo gene transfer involves introducing the DNA into the cells of the patient when the cells are within the patient. In vivo gene transfer also involves introducing the DNA specifically into the ocular endothelial cells of the patient using gene therapy vectors containing endothelial specific promoters. All three of the broad-based categories described above may be used to achieve gene transfer in vivo, ex vivo and in vitro.

Mechanical (i.e., physical) methods of DNA delivery can be achieved by microinjection of DNA into germ or somatic cells, pneumatically delivered DNA-coated particles such as the gold particles used in a "gene gun" and inorganic chemical approaches such as calcium phosphate transfection. It has been found that physical injection of plasmid DNA into muscle cells yields a high percentage of cells which are transfected and have sustained marker genes. The plasmid DNA may or may not integrate into the genome of cells. Non-integration of the transfected DNA would allow the transfection and expression of gene product proteins in terminally differentiated, non-proliferative tissues for a prolonged period of time without fear of mutational insertions, deletions or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer may also be employed for injecting DNA into cells, tissues and organs. With a particle bombardment device, or "gene gun," a motive force is generated to accelerate DNA-coated high density particles (such as gold or tungsten) to a high velocity that allows penetration of the target organs, tissues or cells. Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. The techniques of particle-mediated gene transfer and electroporation are well known to those of ordinary skill in the art Chemical methods of gene therapy involve carrier-mediated gene transfer through the use of fusogenic lipid vesicles such as liposomes or other vesicles for membrane fusion. A carrier harboring a DNA or protein of interest can be conveniently introduced into body fluids or the bloodstream and then site specifically directed to the target organ or tissue in the body. Cell or organ-specific DNA-carrying liposomes, for example, can be developed and the foreign DNA carried by the liposome absorbed by those specific cells. Injection of immunoliposomes that are targeted to a specific receptor on certain cells can be used as a convenient method of inserting the DNA into the cells bearing that receptor. Another carrier system that has been used is the asialoglycoprotein/polylysine conjugate system for carrying DNA to hepatocytes for in vivo gene transfer.

Transfected DNA may also be complexed with other kinds of carriers so that the DNA is carried to the recipient cell and then deposited in the cytoplasm or in the nucleoplasm. DNA can be coupled to carrier nuclear proteins in specifically engineered vesicle complexes and carried directly into the nucleus.

Carrier mediated gene transfer may also involve the use of lipid-based compounds which are not liposomes. For example, lipofectins and cytofectins are lipid-based positive ions that bind to negatively charged DNA and form a complex that can ferry the DNA across a cell membrane. Another method of carrier mediated gene transfer involves receptor-based endocytosis. In this method, a ligand (specific to a cell surface receptor) is made to form a complex with a gene of interest and then injected into the bloodstream. Target cells that have the cell surface receptor will specifically bind the ligand and transport the ligand-DNA complex into the cell.

Biological gene therapy methodologies employ viral vectors to insert genes into cells. Viral vectors that have been used for gene therapy protocols include, but are not limited to, retroviruses, other RNA viruses such as poliovirus or Sindbis virus, adenovirus, adeno-associated virus, herpes viruses, SV 40, vaccinia, lentivirus, and other DNA viruses. Replication-defective murine retroviral vectors are the most widely utilized gene transfer vectors. Murine leukemia retroviruses are composed of a single strand RNA completed with a nuclear core protein and polymerase (pol) enzymes encased by a protein core (gag) and surrounded by a glycoprotein envelope (env) that determines host range. The genomic structure of retroviruses include gag, pol, and env genes enclosed at the 5' and 3' long terminal repeats (LTRs). Retroviral vector systems exploit the fact that a minimal vector containing the 5' and 3' LTRs and the packaging signal are sufficient to allow vector packaging and infection and integration into target cells providing that the viral structural proteins are supplied in trans in the packaging cell line.

Fundamental advantages of retroviral vectors for gene transfer include efficient infection and gene expression in most cell types, precise single copy vector integration into target cell chromosomal DNA and ease of manipulation of the retroviral genome. For example, altered retrovirus vectors have been used in ex vivo methods to introduce genes into peripheral and tumor-infiltrating lymphocytes, hepatocytes, epidermal cells, myocytes or other somatic cells (which may then be introduced into the patient to provide the gene product from the inserted DNA).

The adenovirus is composed of linear, double stranded DNA complexed with core proteins and surrounded with capsid proteins. Advances in molecular virology have led to the ability to exploit the biology of these organisms to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell-free virion so injection of producer cell lines are not necessary. Another potential advantage to adenoviral vectors is the ability to achieve long term expression of heterologous genes in vivo.

Viral vectors have also been used to insert genes into cells using in vivo protocols. To direct tissue-specific expression of foreign genes, cis-acting regulatory elements or promoters that are known to be tissue-specific may be used. This could also involve using gene therapy vectors containing endothelial specific promoters for purposes of targeting blood vessels. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus-infected surrounding cells, in turn, also expressed the gene product. A viral vector can be delivered directly to the in vivo site (by catheter, for example) thus allowing only certain areas to be infected by the virus and providing long-term, site-specific gene expression. In vivo gene transfer using retrovirus vectors has also been demonstrated in mammary tissue and hepatic tissue by injection of the altered virus into blood vessels leading to the organs.

When used in the above or other treatments, a therapeutically effective amount of one of the compounds of the present invention may be employed in pure form or, where such forms exist, in pharmaceutically acceptable salt form and with or without a pharmaceutically acceptable excipient. A "therapeutically effective amount" of the compound of the invention means a sufficient amount of the compound to limit tumor growth or to slow or block tumor metastasis at a reasonable benefit/risk ratio applicable to any medical treatment. It will be understood, however, that the total daily usage of the compounds and compositions of the present invention will be decided by the attending physician within the scope of sound medical judgment.

The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of the compound at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose.

Gene therapy also contemplates the production of a protein or polypeptide where the cell has been transformed with a genetic sequence that turns off the naturally occurring gene encoding the protein, i.e., endogenous gene-activation techniques.

Exogenous Therapy

A safe and effective amount of the tbdn-1 agent is defined as an amount, which would cause the desired therapeutic effect in a patient while minimizing undesired side effects. The dosage regimen will be determined by skilled clinicians, based on factors such as the exact nature of the condition being treated, the severity of the condition, the age and general physical condition of the patient, and so on.

The ophthalmic compositions of the present invention will include one or more tbdn-1 agents and a pharmaceutically acceptable vehicle for said compound(s). Various types of vehicles may be used. The vehicles will generally be aqueous in nature. Aqueous solutions are generally preferred, based on ease of formulation, as well as a patients' ability to easily administer such compositions by means of instilling one to two drops of the solutions in the affected eyes. However, the compounds of formula (I) may also be readily incorporated into other types of compositions, such as suspensions, viscous or semi-viscous gels or other types of solid or semi-solid compositions. Suspensions may be preferred for the tbdn-1 agents which are relatively insoluble in water. The ophthalmic compositions of the present invention may also include various other ingredients, such as buffers, preservatives, co-solvents and viscosity building agents.

The tbdn-1 agents may be contained in various types of pharmaceutical compositions, in accordance with formulation techniques known to those skilled in the art. For example, the tbdn-1 agents may be included in solutions, suspensions and other dosage forms adapted for topical application to the involved tissues, such as tissue irrigating solutions. An appropriate buffer system (e.g., sodium phosphate, sodium acetate or sodium borate) may be added to prevent pH drift under storage conditions.

Ophthalmic products are typically packaged in multidose form. Preservatives are thus generally required to prevent microbial contamination during use. Examples of suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art. Such preservatives are typically employed at a level of from about 0.001 to about 1.0 percent by weight, based on the total weight of the composition (wt. %).

Some of the tbdn-1 agents may have limited solubility in water and therefore may require a surfactant or other appropriate co-solvent in the composition. Such co-solvents include: polyethoxylated castor oils, Polysorbate 20, 60 and 80; Pluronic Registered TM F-68, F-84 and P-103 (BASF Corp., Parsippany N.J., USA); cyclodextrin; or other agents known to those skilled in the art. Such co-solvents are typically employed at a level of from about 0.01 to about 2 wt. %.

The use of physiologically balanced irrigating solutions as pharmaceutical vehicles for the tbdn-1 agents is preferred when the compositions are administered intraocularly. As used herein, the term "physiologically balanced irrigating solution" means a solution which is adapted to maintain the physical structure and function of tissues during invasive or noninvasive medical procedures. This type of solution will typically contain electrolytes, such as sodium, potassium, calcium, magnesium and/or chloride; an energy source, such as dextrose; and a buffer to maintain the pH of the solution at or near physiological levels. Various solutions of this type are known (e.g., Lactated Ringers Solution). BSS Registered TM Sterile Irrigating Solution and BSS Plus Registered TM Sterile Intraocular Irrigating Solution (Alcon Laboratories, Inc., Fort Worth, Tex., USA) are examples of physiologically balanced intraocular irrigating solutions. The latter type of solution is described in U.S. Pat. No. 4,550,022 (Garabedian, et al.), which is incorporated by reference.

In general, the doses utilized for the above-described purposes will vary, but will be in an effective amount to inhibit or reduce neovascularization. As used herein, the term "pharmaceutically effective amount" to inhibit or reduce neovascularization, is that amount which inhibits formation of new blood vessels or reduces the number of blood vessels which are involved in the pathological condition. The doses utilized for any of the above-described purposes will generally be from about 0.01 to about 100 milligrams per kilogram of body weight (mg/kg), administered one to four times per day. When the compositions are dosed topically, they will generally be in a concentration range of about 0.001 wt. % to about 5 wt. %, with 1–2 drops administered 1–5 times per day.

The specific type of formulation selected will depend on various factors, such as the tbdn-1 agent being used, the dosage frequency, and the location of the neovascularization being treated. Topical ophthalmic aqueous solutions, suspensions, ointments, and gels are the preferred dosage forms for the treatment of neovascularization in the front of the eye (the cornea, iris, trabecular meshwork); or neovascularization of the back of the eye if the tbdn-1 agent can be formulated such that it can be delivered topically and the agent is able to penetrate the tissues in the front of the eye. The tbdn-1 agent will normally be contained in these formulations in an amount which will be determined to approximate the natural level of tbdn-1 in normal ocular blood vessels. Preferable concentrations range from about 0.1 to about 5.0 weight/percent. Thus, for topical administration, these formulations are delivered to the surface of the eye one to several times a day, depending on the routine discretion of the skilled clinician. Systemic administration, for example, in the form of tablets is useful for the treatment of neovascularization particularly of the back of the eye, for example, the retina.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from about 0.01 to about 2 wt. %.

As indicated above, use of the tbdn-1 agents to prevent or reduce angiogenesis in ophthalmic tissues is a particularly important aspect of the present invention. The tbdn-1 agents may also be used as an adjunct to ophthalmic surgery, such as by vitreal or subconjunctival injection following ophthalmic surgery. The tbdn-1 agents may be used for acute treatment of temporary conditions, or may be administered chronically, especially in the case of degenerative disease. The compounds may also be used prophylactically, especially prior to ocular surgery or noninvasive ophthalmic procedures, or other types of surgery.

EXAMPLES

Cell Culture

RF/6A rhesus macaque choroid-retina endothelial cells (33, 34) were obtained from the American Type Culture Collection (Manassas, Va.), and were grown in DMEM supplemented with 10% fetal bovine serum (FBS) plus 2 mM glutamine and non essential amino acids. The spontaneously immortalized RF/6A choroid-retina endothelial cell line, derived from the choroid-retina of a rhesus macaque, retains the expression of endothelial markers (33, 34) including the VEGFR-2 tyrosine kinase (our unpublished observation). Human umbilical vein endothelial cells (HUVEC) were obtained from Clonetics (San Diego, Calif.) and grown in DMEM plus 10% FBS, 2mM glutamine, 1 ng/ml bFGF, and a mixture of insulin, transferrin and selinium (Gibco). The IEM cell line, from which tbdn-1 was originally isolated, was grown as previously described (35) and was initially derived by immortalizing differentiation products of embryonic stem cell cultures using SV40 large T antigen. The IEM line expresses endothelial markers and can be induced to form capillary structures in Matrigel after induction with bFGF and leukemia inhibitory factor (35). IEM cells can also contribute to vascular structures in embryonic chimeras in vivo after blastocyst injections (35). Tbdn-1 RNA and protein become downregulated as IEM cells differentiate into capillaries on Matrigel (35).

Capillary Formation

For capillary induction, cultures of RF/6A cells were treated with 10 ng/ml bFGF plus 10 ng/ml VEGF for 48 hours before being transferred to Matrigel (Collaborative, Bedford, Mass.) for a further 96 hours for capillary formation as previously described (32, 35, 36). RF/6A capillary colonies were collected by gently lifting the colonies, together with the Matrigel on which they were growing, from the culture dishes using a fine spatula. Control cultured RF/6A cells were harvested from tissue culture dishes by scraping the cells from the dishes and collected by gentle centrifugation. The pellets of cultured RF/6A cells and the RF/6A capillary colonies were then fixed in 4% buffered paraformaldehyde and immobilized by embedding in small blocks of low melting temperature agarose. The agarose blocks containing the pellets of cultured RF/6A cells and the RF/6A capillary colonies were next fixed in 4% paraformaldehyde and embedded in paraffin blocks for histical processing and analysis.

Anti-tbdn-1 Antibody

An anti-tbdn-1 IgY antibody (Ab1272) was generated by immunizing chickens with a KLH-conjugated 10 mer peptide sequence in the tbdn-1 ORF(13). The peptide sequence used was MDEAQALDTA (tbdn-1 aa 160–170). The IgY was isolated to 90% purity from preimmune and immune egg yolks using Eggstract (Promega).

Tissue Specimens and Immunocytochemistry

Immunocytochemistry was performed on paraformaldehyde fixed, paraffin embedded sections of cultures of untreated RF/6A cells, RF/6A capillary colonies and human eye tissues to detect tbdn-1 and endothelial marker expression. A total of 4 normal human adult eye specimens and 5 specimens from patients with PDR were studied. All human eye tissue specimens were obtained postmortem from consenting donors under the approval of the Institutional Review Boards of the Smith Kettlewell Eye Research Institute, San Francisco and Childrens Hospital Medical Center, Cincinnati. All research on human specimens followed the tenets of the Declaration of Helsinki at all times. Specimens were sectioned, deparaffinized, rehydrated and subjected to immunocytochemistry. All conditions and procedures for processing RF/6A cells and RF/6A capillary colonies were identical. Following a 1 hour blocking step in 2% normal goat serum, sections were incubated with either a 1/100 dilution of chicken anti-tbdn-1 IgY (Ab1272; [32]) or an equal concentration of preimmune IgY. For an endothelial cell marker, rabbit anti-Von Willibrand Factor (Dako, Denmark) was used for labeling endothelial cells in blood vessels in adjacent sections. Anti-tubulin mouse monoclonal antibody (Sigma, St Louis, Mich.) was used as a positive ubiquitous staining control for RF/6A cells and capillary colonies. After rinsing in phosphate buffered saline (PBS), reactions were developed using the appropriate alkaline phosphatase conjugated species specific secondary reagents (anti-rabbit IgG, anti-mouse IgG or anti-chicken IgY; Promega and Vector Laboratories). Red color reactions were generated using naphthol-AS-MX Phosphate in the presence of Fast Red and Levamisole (to block endogenous tissue alkaline phosphatase activity). Slides were then counterstained lightly using a 0.5% aqueous solution of methyl green. Sections were then rinsed, dried and mounted in Permount (Fisher, Pittsburgh, Pa.) prior to viewing and photography using a microscope mounted Kodak DC120 digital camera.

Western Blotting

Cell lysates were prepared using Triton-X 100 lysis buffer (50 mM Tris, pH 8.0, 150 mM NaCl, 1% Triton-X 100) supplemented with protease inhibitors (1 mM PMSF, 0.3 U/ml aprotinin, and 10 ug/ml leupeptin) and phosphatase inhibitors (1 mM sodium orthovanadate, 25 mM sodium fluoride, and 10 mM beta-glycerophosphate). Lysates were clarified by centrifugation, the protein concentration was quantified and samples analyzed by SDS-PAGE. Western blotting was performed by standard procedures using chemiluminescence detection (ECL Plus reagent, Amersham), except for low salt buffer (25 MM NaCl) conditions for Ab1272 incubations and washes. For experiments demonstrating the specificity of the Ab1272 antibody in western blots of RF/6A cells, RF/6A cell clones overexpressing tbdn-1 cDNA sequences 1-1413 in an antisense orientation were generated using zeocin selection from the pcDNA3.1/Zeo vector (Invitrogen). Lysates were prepared from several of these antisense tbdn-1 RF/6A transfectants and from parental RF/6A cells as described above and then used in western blotting experiments for testing the specificity of Ab1272 in detecting tbdn-1 in RF/6A cells.

Results

Tbdn-1 Expression in Endothelial Cells

Figure 1:
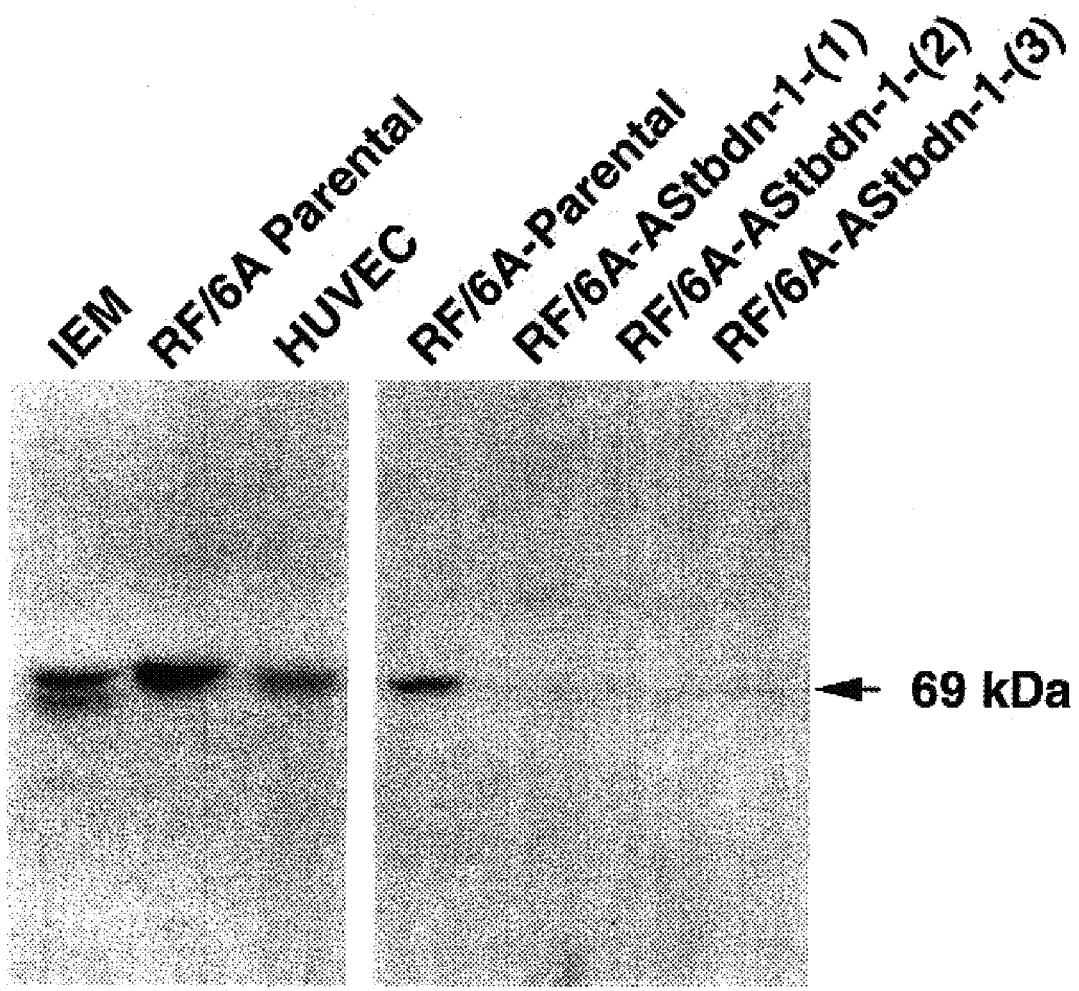
FIG. 1. Tbdn-1 can be specifically detected by anti-tbdn-1 Ab1272 antibody in mouse and human vascular endothelial cells and in rhesus macaque choroid-retina endothelial cells. Expression analysis of tbdn-1 protein in 50 ug of whole cell lystate of the mouse IEM embryonic vascular endothelial cell line (IEM), the untrasfected rhesus RF/6A choroid-retina endothelial cell line (RF/6A Partental), human umbilical vein endothelial cells (HUVEC) and in 3 separate clones of RF/6A cells stably expressing a tbdn-1 antisense cDNA fragment (RF/6A-AStbdn-1), as indicated. The 69 kDa tbdn-1 band, which resolves as a doublet in the IEM cells (12), is indicated by the arrow.

A comparison of tbdn-1 expression in endothelial cell lines from different species is first made. In order to establish that tbdn-1 is equally detectable by Ab1272 anti-tbdn-1 antibody in primate and human retinal endothelial cells as it is in mouse vascular endothelial cells (32), western blotting is performed using the Ab1272 antibody on whole cell lysates prepared from the rhesus macaque RF/6A choroid-retina endothelial cell line (33, 34), the mouse IEM embryonic endothelial cell line (32, 35) and human umbilical vein endothelial cells (HUVEC). Western blotting indicates the presence of a 69 kDa tbdn-1 protein band in all of these endothelial cell lines (FIG. 1, left panel). Ab1272 western analysis of several RF/6A cell clones stably overexpressing an antisense tbdn-1 cDNA fragment, which was designed to block endogenous tbdn-1 expression, shows a significant decrease or complete absence of the 69 kDa band representing tbdn-1 (FIG. 1, right panel). These results indicate that the Ab1272 antibody is specific for detecting tbdn-1 protein in RF/6A cells. The marked decrease of the tbdn-1 band in RF/6A cells harboring tbdn-1 antisense cDNA is similar to IEM cells harboring antisense tbdn-1 cDNA (32). These results indicate that tbdn-1 can be specifically detected by Ab1272 in primate choroid-retina endothelial cells as well as in mouse and human endothelial cells.

Tbdn-1 Expression Pattern in Developing Mouse and Human Vitreal Vasculature

Figure 2:
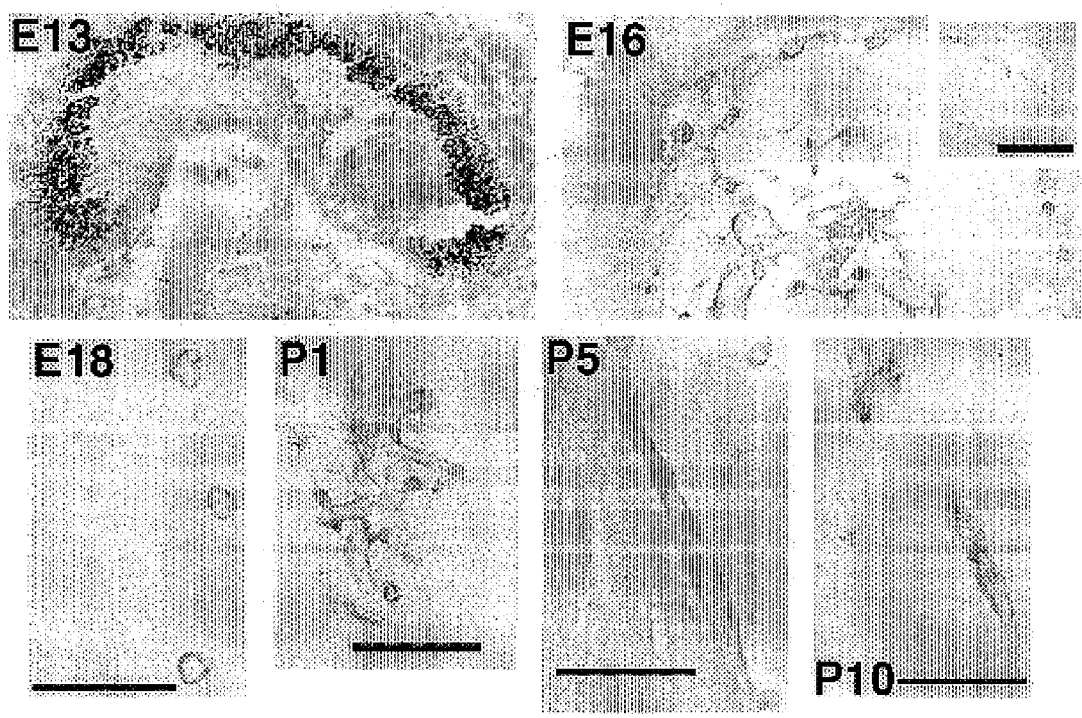
FIG. 2. Tbdn-1 expression in the developing mouse ocular vitreal vasculature. A, Tbdn-1 staining in the developing mouse eye at day 13 of gestation (arrows indicate the early developing hyaloid network). B, Tbdn-1 staining in the hyaloid vascular network of developing eye from a day 16 gestation mouse embryonic eye (arrows indicate the hyaloid vascular network). Inset in B, an adjacent section stained with preimmune IgY, which is a negative control for the anti-tbdn-1 antibody staining, showing no staining. C, Tbdn-1 staining in cross sections of vitreal blood vessels in the gestational day 18 embryonic eye (arrows indicate that the highest levels of tbdn-1 positivity are in the vitreal vascular endothelial cells). D, Tbdn-1 staining in a tuft of endothelial cells (arrowed) of the vitreal vasculature in the postnatal day 1 mouse eye. E, Tbdn-1 staining in sections of vitreal vasculature in the postnatal day 5 mouse eye. F, Tbdn-1 staining in sections of vitreal vasculature in the postnatal day 10 mouse eye. nr, neural retina; le, lens; arrows in all panels indicate vitreal blood vessels; scale bars equal 50 um.

Tbdn-1 immunolocalization was performed on developing mouse eye specimens in order to study the temporal dynamics and spatial localization of tbdn-1 expression in the developing posterior chamber ocular vasculature. Analysis of mouse embryonic eye posterior chambers revealed that tbdn-1 expression was low in newly emerging vitreal blood vessels at embryonic day 13 (FIG. 2). At later stages of vitreal vascular network maturation, tbdn-1 was expressed at higher levels (see FIG. 2). The embryonic vitreal vascular networks were negative when stained with preimmune IgY, a negative control for the tbdn-1 antibody (FIG. 2). Hyalocytes scattered within and around the vitreal vascular networks at the E16 and E18 stages also expressed tbdn-1 at the same levels as found in vitreal blood vessel endothelial cells. Postnatally, tbdn-1 expression levels remain high at P1 (FIG. 2), but showed a decrease between P5 and P10 stages (FIG. 2). These results indicate that vitreal vascular tbdn-1 expression peaks during mid to late gestation as the embryonic vitreal vasculature matures during development.

Figure 3:
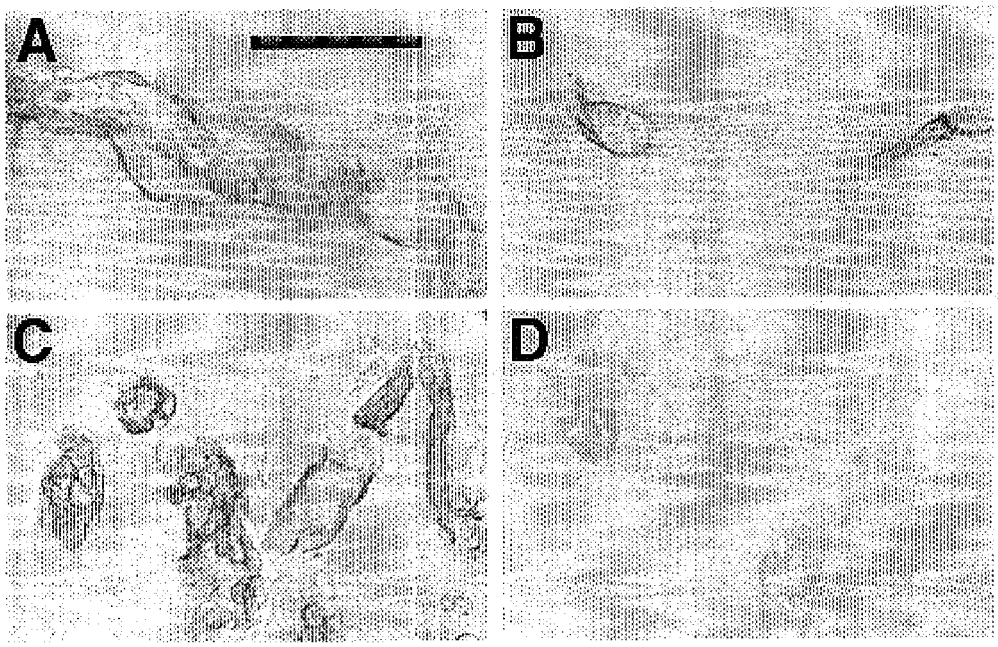
FIG. 3. Tbdn-1 and vascular marker expression in the developing human ocular vitreal vasculature.

Tbdn-1 immunolocalization was also performed on a human embryonic eye specimen obtained at autopsy at approximately 14 weeks of gestation in order to study the spatial localization of tbdn-1 expression in the developing human ocular vitreal vasculature. Analysis of the 14 week human embryonic eye revealed that tbdn-1 was also expressed at high levels in human vitreal vessels (FIG. 3). The human embryonic vitreal vascular networks also expressed the endothelial marker Von Willibrand Factor (FIG. 3) and were negative when stained with preimmune IgY, a negative control for the tbdn-1 antibody (FIG. 3). As observed in mouse, hyalocytes scattered within and around the vitreal vascular networks in human embryonic eyes also expressed tbdn-1 at the same levels found in vitreal endothelial lining cells.

Tbdn-1 Expression in Ocular Endothelial Homeostasis in Adult

Tbdn-1 immunolocalization is performed on normal adult human eye specimens in order to determine the levels of tbdn-1 expression in normal adult ocular blood vessels. In normal human adult eye specimens, both limbic blood vessels (FIG. 4) and retinal blood vessels (FIG. 4) show high levels of tbdn-1 expression in the endothelial cells lining these vessels. A very similar pattern of tbdn-1 expression was detected in normal choroidal blood vessel endothelium. The limbic and retinal blood vessels in normal adult human specimens shows the same staining pattern using an anti-Von Willibrand Factor antibody (retinal vessels are shown in FIG. 4), while adjacent sections incubated with either normal rabbit serum or preimmune IgY controls show no staining (an IgY reacted section is shown in FIG. 4). These results indicate that, in contrast to most vascular beds, tbdn-1 is expressed at high levels in endothelial linings of normal adult ocular blood vessels during homeostasis.

Tbdn-1 Expression is Suppressed During Capillary Formation of a Choroid-retina Endothelial Cell Line As we have described previously, IEM cells display a 69 kDa doublet which could correspond to acetylated and unacetylated forms of tbdn-1. Furthermore, Ab1272 western analysis of several RF/6A cell clones stably overexpressing an antisense tbdn-1 cDNA fragment, which was designed to block endogenous tbdn-1 expression, showed a significant decrease or complete absence of the 69 kDa band representing tbdn-1 (FIG. 1, right panel). These results indicate that the Ab1272 antibody is specific for detecting tbdn-1 protein in RF/6A cells. The marked decrease of the tbdn-1 band in RF/6A cells harboring tbdn-1 antisense cDNA is similar to what we had previously shown using IEM cells harboring antisense tbdn-1 cDNA. These results indicate that tbdn-1 can be specifically detected by Ab1272 in primate choroid-retina endothelial cells as well as in mouse and human endothelial cells. Our previous work has shown that tbdn-1 protein expression is downregulated during capillary formation of the IEM embryonic vascular endothelial cell line in vitro. Since tbdn-1 expression is maintained at high levels in adult ocular blood vessels, contrary to most other vascular beds, we tested here whether or not tbdn-1 was regulated in a manner different from IEM cells using a model of choroid-retina endothelial cell capillary outgrowth in vitro. We have previously developed an in vitro capillary formation assay using the IEM cell line and have used the RF/6A endothelial cell line derived from rhesus choroid-retina tissue for a similar application here. By treating either IEM or RF/6A cells with angiogenic growth factors and then plating the stimulated cells onto a layer of Matrigel, we can reproducibly generate colonies of cells sprouting capillary structures (FIG. 5). These capillary colonies can then be fixed, embedded and histologically sectioned for immunocytochemical studies as we have previously described for IEM capillary colonies. Interestingly, little to no staining for tbdn-1 protein was detected in histological sections of fixed, paraffin embedded RF/6A cultures induced to form capillary outgrowths in Matrigel (FIG. 5). However, high levels of tbdn-1 expression were present in histological sections of fixed, paraffin embedded RF/6A cells maintained in tissue culture in the absence of any treatment for 48 hours (FIG. 5). Detection of alpha tubulin immunostaining in sections of the preparations of RF/6A capillary cultures (inset in FIG. 5) confirmed retention of antigenicity in these fixed, paraffin embedded and sectioned capillary colony preparations. These results show that a suppression of tbdn-1 expression accompanies the induction of capillary formation of RF/6A choroid-retina endothelial cells, in a similar manner as observed during capillary outgrowth of the IEM cells.

Tbdn-1 Expression is Suppressed in Retinal Neovascularization in Proliferative Diabetic Retinopathy (PDR)

Tbdn-1 immunolocalization was performed on diabetic adult human eye specimens in parallel with the normal samples in order to determine if the expression characteristics of tbdn-1 in retinal blood vessels change during proliferative diabetic retinopathy (PDR). Sections of 5 out of 5 specimens of eyes from patients with PDR which were processed and stained simultaneously with the normal human eye samples showed a dramatic decrease in expression of endothelial tbdn-1 protein levels in diseased, neovascularized areas of the retinas. Tbdn-1 was downregulated or completely absent from abnormal proliferating blood vessels and fronds in both preretinal membranes and neural retinal areas in the PDR specimens (see FIG. 4 for several representative specimens). However, PDR specimens showed no change in tbdn-1 levels in the limbic vessels in the anterior portion of the eye in the same sections (FIG. 6). Thus, the suppression of tbdn-1 expression occurs in blood vessels within the neural retina and preretinal membranes but does not occur in limbic vessels in the anterior portions of the same PDR specimens. The limbic vessel expression of tbdn-1 in PDR also served as an internal positive control for tbdn-1 expression in these specimens. We also observed that tbdn-1 was downregulated in the choroidal vessels in the PDR specimens in comparison to choroidal vessels in normal specimens (data not shown). Expression of the endothelial marker Von Willibrand Factor was detected at high levels, similar to normal retinal blood vessels, in blood vessels showing decreased tbdn-1 expression from the same PDR specimens (FIG. 6). These results indicate that tbdn-1 expression is suppressed in abnormal proliferating blood vessels of the neural retina and preretinal membranes in PDR.

Inhibition of tbdn-1 Expression Levels Augments Capillary Outgrowth in Vitro

Since tbdn-1 is an intracellular molecule with a regulatory function rather than an extracellular cytokine or soluble factor, we rationalized that the most useful approach to testing its function in capillary outgrowth would be to block its expression in endothelial cell lines. Therefore, we tested of tbdn-1 could play a role in capillary outgrowth response in vitro after inhibiting tbdn-1 protein expression levels using an antisense cDNA in both IEM embryonic endothelial cells and in RF/6A choroid-retina endothelial cells. In order to verify that an antisense tbdn-1 cDNA blocked tbdn-1 protein expression, western blotting and acetyltransferase assays were performed on lysates of IEM and RF/6A cell clones stably overexpressing the antisense tbdn-1 cDNA. The stable overexpression of antisense tbdn-1 cDNA inhibited tbdn-1 protein expression levels in both IEM embryonic endothelial cells and in RF/6A choroid-retina endothelial cells (see FIG. 1). Furthermore, RF/6A clones stably overexpressing antisense tbdn-1 cDNA also show a significantly decreased acetyltransferase activity associated with IPs of tbdn-1 prepared from these cells (FIG. 7).

We next tested the effects of altering tbdn-1 expression on capillary formation using an in vitro capillary formation assay in Matrigel. RF/6A cells overexpressing antisense tbdn-1 cDNA show a significantly augmented capillary outgrowth response (FIG. 8). Capillary colonies formed by RF/6A AS-tbdn-1 cDNA transfectant clones show longer, more complex and more abundant capillary sprouts than vector controls. Overexpression of antisense tbdn-1 cDNA also augmented capillary outgrowth of IEM cells (not shown).

It is possible that overexpression of antisense tbdn-1 cDNA may lead to the production of toxic or aberrant proteins which could cause a nonspecific change in endothelial capillary outgrowth. In order to address this possibility, we have confirmed using in vitro translation methodology that the AS-tbdn-1 construct does not encode an irrelevant protein product which could be nonspecifically toxic to the endothelial cells (data not shown).

References

1) L. Diaz-Flores et al., Angiogenesis: an Update, Histology and Histopathology, volume 9, pages 807–843 (1994).
2) Folkman, J. (1995) Clinical applications of research on angiogenesis. New Eng. J. Med. 333, 1757–1763.
3) Battegay, E. J. (1995) Angiogenesis: mechanistic insights, neovascular diseases, and therapeutic prospects. J. Mol. Med., 73, 333–346.
4) Johnston, M. C., Noden, D. M., Hazelton, R. D., Coulombre, J. L., Coulombre, A. J. (1979) Origins of avian ocular and periocular tissues. Exp. Eye Res. 29, 27–43.
5) Bahn, C. F., Falls, H. F., Varley, G. A., Meyer, R. F., Edelhauser, H. F., Bourne, W. M. (1984) Classification of corneal endothelial disorders based on neural crest origin. Ophthalmology 91, 558–563.
6) Reese, A. B., Owens, W. C. (1955) Symposium: Retrolental Fibroplasia (Retinopathy of Prematurity). Am. J. Opthalmol. 40, 151–165.
7) Reese, A. B., King, M. J., Owens, W. C. (1953) A classification of retrolental fibroplasia. Am. J. Opthalmol. 10, 1331–1333.
8) Tasman, W. (1970) Vitreoretinal changes in cicatricial retrolental fibroplasia. Trans. Am. Ophthalmol. Soc. 68, 548–594.
9) Tysinger, J. W. Jr., Weidenthal, D. T. (1977) Nasal heterotopia of the macula in retinopathy of prematurity. Am. J. Ophthalmol. 83, 499–500.
10) Tasman, W. (1975) Macular changes in congenital retinoschisis. Mod. Probl. Ophthalmol. 15, 40–49.
11) Harris, G. S. (1976) Retinopathy of prematurity and retinal detachment. Can. J. Ophthalmol. 11, 21–25.
12) Kalina, R. E. (1980) Treatment of retrolental fibroplasia. Surv. Ophthalmol. 24, 229–236.
13) Tasman, W. (1979) Late complications of retrolental fibroplasia. Ophthalmology 86, 1724–1740.
14) Hittner, H. M., Rhodes, L. M., McPherson, A. R. (1979) Anterior segment abnormalities in cicatricial retinopathy of prematurity. Ophthalmology 86, 803–816.
15) Kushner, B. J. (1982) Strabismus and amblyopia associated with regressed retinopathy of prematurity. Arch Ophthalmol 100, 256–261.
16) Nissenkorn, I., Yassur, Y., Mashkowski, D., Sherf, I., Ben-Sira, I. (1983) Myopia in premature babies with and without retinopathy of prematurity. Br. J. Ophthalmol. 67,170–173.
17) Kushner, B. J., Sondheimer, S. (1982) Medical treatment of glaucoma associated with cicatricial retinopathy of prematurity. Am. J. Ophthalmol. 94, 313–317.

18) Dobson, V., Quinn, G. E., Saunders, R. A., Spencer, R., Davis, B. R., Risser, J., Palmer, E. A. (1995) Grating visual acuity in eyes with retinal residua of retinopathy of prematurity. The Cryotherapy for Retinopathy of Prematurity Cooperative Group. Arch. Ophthalmol. 113, 1172–1177.

19) Infeld, D. A., O'Shea, J. G. (1998) Diabetic retinopathy. Postgrad. Med. J. 74, 129–133.

20) Kohner, E M., (1993) Diabetic Retinopathy. BMJ, 307, 1195–1199.

21) Paques M, Massin P, Gaudric A (1997) Growth factors and diabetic retinopathy. Diabetes Metab 23(2):125–30.

22) Pfeiffer, A., Spranger, J., Meyer-Schwickerath, R., Schatz, H. (1997) Growth factor alterations in advanced diabetic retinopathy: a possible role of blood retina barrier breakdown. Diabetes 46, Suppl 2, S26–30.

23) Robinson, G. S., Aiello, L. P. (1998) Angiogenic factors in diabetic ocular disease: mechanisms of today, therapies for tomorrow. Int. Ophthalmol. Clin. Spring 38, 89–102.

24) Natarajan, R., Bai, W., Lanting, L., Gonzales, N., Nadler, J. (1997) Effects of high glucose on vascular endothelial growth factor expression in vascular smooth muscle cells. Am. J. Physiol. 273, H2224–2231.

25) Hammes, H. P., Lin, J., Bretze, R. G., Brownlee, M., Breier, G. (1998) Upregulation of the vascular endothelial growth factor/vascular endothelial growth factor receptor system in experimental background diabetic retinopathy of the rat. Diabetes 47, 401–406.

26) Amin, R. H., Frank, R. N., Kennedy, A., Eliott, D., Puklin, J. E., Abrams, G. W. (1997) Vascular endothelial growth factor is present in glial cells of the retina and optic nerve of human subjects with nonproliferative diabetic retinopathy. Invest. Ophthalmol. Vis. Sci. 38, 36–47.

27) Kvanta, A. (1995) Expression and regulation of vascular endothelial growth factor in choroidal fibroblasts. Curr. Eye Res. 14, 1015–1020.

28) Crum, et al., A New Class of Steroids Inhibits Angiogenesis in the Presence of Heparin or a Heparin Fragment, Science, volume 230, pages 1375–1378 (1985). 29) Kitazawa, Increased Intraocular Pressure Induced by Corticosteroids, American Journal of Ophthalmology, volume 82, pages 492–493 (1976).

30) S. Taylor, Protamine is an Inhibitor of Angiogenesis, Nature, volume 297, pages 307–312 (1982).

31) European Journal of Pharmacology, volume 178, pages 247–250 (1990).

32) Gendron, R. L., Adams., L. C., and Paradis, H. Tubedown-1, a novel Acetyltransferase Associated with Blood Vessel Development., *Develop Dyn.*, May 24, 2000.

33) Lou, D. A., Hu, F. N. Co-distribution of von Willebrand factor and fibronectin in cultured rhesus endothelial cells. Histochem. J., 1987, 19, 431–438.

34) Lou, D. A., Hu, F. N. Specific antigen and organelle expression of a long-term rhesus endothelial cell line. In Vitro Cell Dev. Biol., 1987, 23, 75–85.

35) Gendron, R. L., Tsai, F.-Y., Paradis, H. and Arceci, R. J. Induction of Embryonic Vasculogenesis by bFGF and LIF in vitro and in vivo. *Dev. Biol.*, 1996, 177, 332–347.

36) Paradis, H., and Gendron, R. L. LIF transduces contradictory signals on capillary outgrowth through induction of Stat3 and $p^{41/43}$ MAP kinase. *J Cell Science*, 2000, 113, 4331–4339.

What is claimed is:

1. An isolated amino acid molecule consisting of the sequence shown in SEQ ID No. 2.

2. An isolated amino acid molecule consisting of the sequence shown in SEQ ID No. 3.

3. An isolated amino acid molecule consisting of the sequence shown in SEQ ID No. 4.

4. An isolated amino acid molecule consisting of the sequence shown in SEQ ID No. 5.

5. A pharmaceutical formulation comprising (a) the isolated amino acid molecule of claim 1, wherein said molecule is biologically active and (b) a pharmaceutically acceptable carrier adapted for administration by either intraocular injection, subretinal injection, subconjunctival injection or by topical administration to an ocular surface.

6. A pharmaceutical formulation comprising (a) the isolated amino acid molecule of claim 2, wherein said molecule is biologically active and (b) a pharmaceutically acceptable carrier adapted for administration by either intraocular injection, subretinal injection, subconjunctival injection or by topical administration to an ocular surface.

7. A pharmaceutical formulation comprising (a) the isolated amino acid molecule of claim 3, wherein said molecule is biologically active and (b) a pharmaceutically acceptable carrier adapted for administration by either intraocular injection, subretinal injection, subconjunctival injection or by topical administration to an ocular surface.

8. A pharmaceutical formulation comprising (a) the isolated amino acid molecule of claim 4, wherein said molecule is biologically active and (b) a pharmaceutically acceptable carrier adapted for administration by either intraocular injection, subretinal injection, subconjunctival injection or by topical administration to an ocular surface.

9. The pharmaceutical formulation of claim 5, wherein the formulation is adapted for administration to treat ocular neovascularization in mammals.

10. The pharmaceutical formulation of claim 6, wherein the formulation is adapted for administration to treat ocular neovascularization in mammals.

11. The pharmaceutical formulation of claim 7, wherein the formulation is adapted for administration to treat ocular neovascularization in mammals.

12. The pharmaceutical formulation of claim 8, wherein the formulation is adapted for administration to treat ocular neovascularization in mammals.

* * * * *

SEQUENCE LISTING

<160> NUMBER OF SEQ ID NOS: 6

<210> SEQ ID NO 1
<211> LENGTH: 3418
<212> TYPE: DNA
<213> ORGANISM: Homo sapiens

<400> SEQUENCE: 1

```
caagtaacac ccgcaagatg atagaggatc tgcagagtga gcatcatgga ttggttatgc      60
tttaccattt attagaagac tatgaaatgg cagcaaaaat tttagaagag tttaggaaaa     120
cacagcgagc atctcctgat aaagtggatt atgaatatag tgaactcctc ttatatcaga     180
atcaagttct tcgggaagca ggtctttata gagaagccct ggaacatctt tgtacctatg     240
aaaagcagat ttgtgataaa cttgctgttg aagaaaccaa aggggaactt ctgttgcagt     300
tgtgtcgttt ggaagatgct gctgacgttt atagaggatt acaagagagg aatcctgaaa     360
attgggccta ttacaaaggc ttagaaaaag cactgaagcc agctaatatg ttagaacggc     420
taaaaatata tgaggaagcc tggactaaat accccagggg actcgtgcca agaaagctgc     480
ccttaaactt tttatctgga gagaagttta aggagtgttt ggataggttc ctaaggatga     540
atttcagcaa gggctgtcca cctgtcttca ataccttgag gtctttatac agagataaag     600
agaaggtggc aatcgtagaa gaactagtag ttggttatga aacttctcta aaaagttgtc     660
gcctatttaa ccccaatgat gatggaaagg aggaacctcc aaccacatta ctttgggtcc     720
agtactattt ggcacagcat tatgataaaa ttggtcagcc atccattgct ctggaataca     780
taaatactgc aattgaaagt acaccaacat tgatagaact ctttcttgta aaagctaaaa     840
```

-continued

```
tctataagca tgctgggaat attaaagaag ctgccaggtg gatggatgaa gcccaggccc    900
tggacacagc agacagattt attaattcca agtgtgcaaa atacatgtta aaagccaacc    960
tgattaaaga ggctgaagaa atgtgttcca agtttacgag ggaaggaact tcagcggtag   1020
agaacctgaa tgaaatgcag tgtatgtggt tccagacaga gtgtgctcag gcatacaaag   1080
caatgaacaa atttggtgaa gcacttaaga aatgtcatga aattgagaga cattttatag   1140
aaatcaccga tgaccagttt gactttcata catactgtat gaggaagatc acccttagat   1200
catatgtgga cttattaaaa ctagaagatg tacttcgaca gcatccattt tacttcaaag   1260
cagcgagaat tgctattgag atctatttga agcttcatga caaccctctg acagatgaga   1320
acaaagaaca cgaggctgat acagcaaaca tgtctgacaa agagctaaag aaactgcgta   1380
ataaacaaag aagagctcaa aagaaagccc agattgaaga agagaaaaaa atgccgaaa    1440 aagaaaagcc gcaacggaat ccgaaaaaga aaaggatga tgatgacgaa gaaattggag    1500
gccccaaaga agagcttatc cctgagaaac tggccaaggt tgaaactcca ttggaagaag   1560
ctattaagtt tttaacacca ttgaagaact tggtgaagaa caagatagaa actcatcttt   1620
ttgcctttga gatctacttt aggaaagaaa agtttctttt gatgctacaa tcagtaaagc   1680
gggcatttgc tattgattct agtcatccct ggcttcatga gtgcatgatt cgactctttc   1740
attctgtgtg tgaaagtaaa gacttacccg aaacagttag aacagtatta aaacaagaaa   1800
tgaatcgtct ttttggagca acaaatccaa agaattttaa tgaaaccttt ctgaaaagga   1860
attctgattc attgccacat agattatcag ctgccaaaat ggtatattat ttagattctt   1920
ctagtcaaaa acgagcaata gagctggcga caacacttga tggatccctc accaacagaa   1980
accttcagac ttgcatggaa gtgttggaag ccttgtgtga tggtagccta cgagactgta   2040
aagaagctgc cgaagcctac agagcaagtt gtcataagct tttccctttat gctttggctt   2100 tcatgcctcc tggatacgaa gaggatatga agatcacagt gaacggagat agttctgcag   2160
aaacggaaga actggccaat gaaatctgaa catcattaaa caagcaaatg gaatgacttt   2220
ggaccatatc tagtgtataa tattttttgtc acgcacctgc tgcattgctc ttacttacac   2280
agaatgagag gagtaaatgt tcttgccttc aaatagtctt acgttttta tcctgctgaa    2340 aactatatat aaaatatcta acattacagg atataggttc agtttcttaa aaaattaaaa   2400
gctgctaaaa ttgagggggtt taaaagaaaa aaaaatccgt atcctattcc taccttccct   2460
tcccatgttt ttaactaatt tatataaaat ctggaggcta taacagctaa catagcaggt   2520
gtgtggcaga atatattactt taaatttgtc ttgtgagatt ttgctatatc tcagacagca   2580
taaataaatg ctgtttttagc actggattct ttcactgagc acaaagagtt gttgggctt    2640 tagcatctgc ctgattctgt tacggggttg gtgattgacc ataggaagta tgcaatgtga   2700
atcactgtgt acagagccgt ctacaacaca tgcttgacgt tgtagagact gggacacata   2760
gctaccaagc ggattaagtg aaacctagaa ggtgttcagt acgtgtgttg tgtttccaaa   2820
attcactgta catgatcagt ttggtgttct tgtaccacag ttttttaaccg aaggaaccag   2880 ttggaacaat ctcaattttaa ctaaaacttg aagaactaaa ataacaatgc aaacctttat   2940
cattgttttg gccaaacttg ttaaaactgt aatgcaagaa ccaaatgcac tgtgatgtgg   3000
caccaactaa ttatgcaagc atgaattttt cacctgagag tgaaaaaaga aaactctacc   3060
atggcttgaa gttacaggag cagaactcct gactaccatt ctatgactga tgaagagact   3120
aatatctaaa acctcagcag gccttgttca cgatatgcag aaaaagtgct gcagtttaga   3180
tacctctggg aacttttcca cagtgtcaca ggtttgtaat acttgaagcc cttcatttct   3240
```

```
aagaatatat ttctcgctca gttgtttcag gcaagcccaa gactttgtaa ttttaaagg    3300 gcccaagatt tttttttcaa taacagacca gcttctttt cctgcagtta caaatgtaat    3360 ttctttttt tttgttgtc aaacataagg taccaaatat gcaataaatt gttttggg      3418
```

<210> SEQ ID NO 2
<211> LENGTH: 593
<212> TYPE: PRT
<213> ORGANISM: Homo sapiens

<400> SEQUENCE: 2

```
Met Leu Glu Arg Leu Lys Ile Tyr Glu Glu Ala Trp Thr Lys Tyr Pro
1               5                   10                  15

Arg Gly Leu Val Pro Arg Lys Leu Pro Leu Asn Phe Leu Ser Gly Glu
            20                  25                  30

Lys Phe Lys Glu Cys Leu Asp Arg Phe Leu Arg Met Asn Phe Ser Lys
        35                  40                  45

Gly Cys Pro Pro Val Phe Asn Thr Leu Arg Ser Leu Tyr Arg Asp Lys
    50                  55                  60

Glu Lys Val Ala Ile Val Glu Glu Leu Val Val Gly Tyr Glu Thr Ser
65                  70                  75                  80

Leu Lys Ser Cys Arg Leu Phe Asn Pro Asn Asp Asp Gly Lys Glu Glu
                85                  90                  95

Pro Pro Thr Thr Leu Leu Trp Val Gln Tyr Tyr Leu Ala Gln His Tyr
            100                 105                 110

Asp Lys Ile Gly Gln Pro Ser Ile Ala Leu Glu Tyr Ile Asn Thr Ala
        115                 120                 125

Ile Glu Ser Thr Pro Thr Leu Ile Glu Leu Phe Leu Val Lys Ala Lys
    130                 135                 140

Ile Tyr Lys His Ala Gly Asn Ile Lys Glu Ala Ala Arg Trp Met Asp
145                 150                 155                 160

Glu Ala Gln Ala Leu Asp Thr Ala Asp Arg Phe Ile Asn Ser Lys Cys
                165                 170                 175

Ala Lys Tyr Met Leu Lys Ala Asn Leu Ile Lys Glu Ala Glu Glu Met
            180                 185                 190

Cys Ser Lys Phe Thr Arg Glu Gly Thr Ser Ala Val Glu Asn Leu Asn
        195                 200                 205

Glu Met Gln Cys Met Trp Phe Gln Thr Glu Cys Ala Gln Ala Tyr Lys
    210                 215                 220

Ala Met Asn Lys Phe Gly Glu Ala Leu Lys Lys Cys His Glu Ile Glu
225                 230                 235                 240

Arg His Phe Ile Glu Ile Thr Asp Asp Gln Phe Asp Phe His Thr Tyr
                245                 250                 255

Cys Met Arg Lys Ile Thr Leu Arg Ser Tyr Val Asp Leu Leu Lys Leu
            260                 265                 270

Glu Asp Val Leu Arg Gln His Pro Phe Tyr Phe Lys Ala Ala Arg Ile
        275                 280                 285

Ala Ile Glu Ile Tyr Leu Lys Leu His Asp Asn Pro Leu Thr Asp Glu
    290                 295                 300

Asn Lys Glu His Glu Ala Asp Thr Ala Asn Met Ser Asp Lys Glu Leu
305                 310                 315                 320

Lys Lys Leu Arg Asn Lys Gln Arg Arg Ala Gln Lys Ala Gln Ile
                325                 330                 335

Glu Glu Glu Lys Lys Asn Ala Glu Lys Glu Lys Pro Gln Arg Asn Pro
            340                 345                 350
```

```
Lys Lys Lys Lys Asp Asp Asp Glu Glu Ile Gly Gly Pro Lys Glu
            355                 360                 365

Glu Leu Ile Pro Glu Lys Leu Ala Lys Val Glu Thr Pro Leu Glu Glu
    370                 375                 380

Ala Ile Lys Phe Leu Thr Pro Leu Lys Asn Leu Val Lys Asn Lys Ile
385                 390                 395                 400

Glu Thr His Leu Phe Ala Phe Glu Ile Tyr Phe Arg Lys Glu Lys Phe
                405                 410                 415

Leu Leu Met Leu Gln Ser Val Lys Arg Ala Phe Ala Ile Asp Ser Ser
            420                 425                 430

His Pro Trp Leu His Glu Cys Met Ile Arg Leu Phe His Ser Val Cys
            435                 440                 445

Glu Ser Lys Asp Leu Pro Glu Thr Val Arg Thr Val Leu Lys Gln Glu
    450                 455                 460

Met Asn Arg Leu Phe Gly Ala Thr Asn Pro Lys Asn Phe Asn Glu Thr
465                 470                 475                 480

Phe Leu Lys Arg Asn Ser Asp Ser Leu Pro His Arg Leu Ser Ala Ala
                485                 490                 495

Lys Met Val Tyr Tyr Leu Asp Ser Ser Gln Lys Arg Ala Ile Glu
            500                 505                 510

Leu Ala Thr Thr Leu Asp Gly Ser Leu Thr Asn Arg Asn Leu Gln Thr
    515                 520                 525

Cys Met Glu Val Leu Glu Ala Leu Cys Asp Gly Ser Leu Arg Asp Cys
530                 535                 540

Lys Glu Ala Ala Glu Ala Tyr Arg Ala Ser Cys His Lys Leu Phe Pro
545                 550                 555                 560

Tyr Ala Leu Ala Phe Met Pro Pro Gly Tyr Glu Asp Met Lys Ile
                565                 570                 575

Thr Val Asn Gly Asp Ser Ser Ala Glu Thr Glu Glu Leu Ala Asn Glu
            580                 585                 590

Ile

<210> SEQ ID NO 3
<211> LENGTH: 723
<212> TYPE: PRT
<213> ORGANISM: Homo sapiens

<400> SEQUENCE: 3

Met Ile Glu Asp Leu Gln Ser Glu His His Gly Leu Val Met Leu Tyr
1               5                   10                  15

His Leu Leu Glu Asp Tyr Glu Met Ala Ala Lys Ile Leu Glu Glu Phe
            20                  25                  30

Arg Lys Thr Gln Gln Thr Ser Pro Asp Lys Val Asp Tyr Glu Tyr Ser
        35                  40                  45

Glu Leu Leu Leu Tyr Gln Asn Gln Val Leu Arg Glu Ala Gly Leu Tyr
    50                  55                  60

Arg Glu Ala Leu Glu His Leu Cys Thr Tyr Glu Lys Gln Ile Cys Asp
65                  70                  75                  80

Lys Leu Ala Val Glu Glu Thr Lys Gly Glu Leu Leu Gln Leu Cys
                85                  90                  95

Arg Leu Glu Asp Ala Ala Asp Val Tyr Arg Gly Leu Gln Glu Arg Asn
            100                 105                 110

Pro Glu Asn Trp Ala Tyr Tyr Lys Gly Leu Glu Lys Ala Leu Lys Pro
        115                 120                 125
```

-continued

```
Ala Asn Met Leu Glu Arg Leu Lys Ile Tyr Glu Glu Ala Trp Thr Lys
    130                 135                 140

Tyr Pro Arg Gly Leu Val Pro Arg Lys Leu Pro Leu Asn Phe Leu Ser
145                 150                 155                 160

Gly Glu Lys Phe Lys Glu Cys Leu Asp Arg Phe Leu Arg Met Asn Phe
                165                 170                 175

Ser Lys Gly Cys Pro Pro Val Phe Asn Thr Leu Arg Ser Leu Tyr Arg
            180                 185                 190

Asp Lys Glu Lys Val Ala Ile Val Glu Glu Leu Val Val Gly Tyr Glu
        195                 200                 205

Thr Ser Leu Lys Ser Cys Arg Leu Phe Asn Pro Asn Asp Asp Gly Lys
    210                 215                 220

Glu Glu Pro Pro Thr Thr Leu Leu Trp Val Gln Tyr Tyr Leu Ala Gln
225                 230                 235                 240

His Tyr Asp Lys Ile Gly Gln Pro Ser Ile Ala Leu Glu Tyr Ile Asn
                245                 250                 255

Thr Ala Ile Glu Ser Thr Pro Thr Leu Ile Glu Leu Phe Leu Val Lys
            260                 265                 270

Ala Lys Ile Tyr Lys His Ala Gly Asn Ile Lys Glu Ala Ala Arg Trp
        275                 280                 285

Met Asp Glu Ala Gln Ala Leu Asp Thr Ala Asp Arg Phe Ile Asn Ser
290                 295                 300

Lys Cys Ala Lys Tyr Met Leu Lys Ala Asn Leu Ile Lys Glu Ala Glu
305                 310                 315                 320

Glu Met Cys Ser Lys Phe Thr Arg Glu Gly Thr Ser Ala Val Glu Asn
                325                 330                 335

Leu Asn Glu Met Gln Cys Met Trp Phe Gln Thr Glu Cys Ala Gln Ala
            340                 345                 350

Tyr Lys Ala Met Asn Lys Phe Gly Glu Ala Leu Lys Lys Cys His Glu
        355                 360                 365

Ile Glu Arg His Phe Ile Glu Ile Thr Asp Asp Gln Phe Asp Phe His
    370                 375                 380

Thr Tyr Cys Met Arg Lys Ile Thr Leu Arg Ser Tyr Val Asp Leu Leu
385                 390                 395                 400

Lys Leu Glu Asp Val Leu Arg Gln His Pro Phe Tyr Phe Lys Ala Ala
                405                 410                 415

Arg Ile Ala Ile Glu Ile Tyr Leu Lys Leu His Asp Asn Pro Leu Thr
            420                 425                 430

Asp Glu Asn Lys Glu His Glu Ala Asp Thr Ala Asn Met Ser Asp Lys
        435                 440                 445

Glu Leu Lys Lys Leu Arg Asn Lys Gln Arg Arg Ala Gln Lys Lys Ala
    450                 455                 460

Gln Ile Glu Glu Glu Lys Lys Asn Ala Glu Lys Glu Lys Pro Gln Arg
465                 470                 475                 480

Asn Pro Lys Lys Lys Asp Asp Asp Glu Glu Ile Gly Gly Pro
                485                 490                 495

Lys Glu Glu Leu Ile Pro Glu Lys Leu Ala Lys Val Glu Thr Pro Leu
            500                 505                 510

Glu Glu Ala Ile Lys Phe Leu Thr Pro Leu Lys Asn Leu Val Lys Asn
        515                 520                 525

Lys Ile Glu Thr His Leu Phe Ala Phe Glu Ile Tyr Phe Arg Lys Glu
    530                 535                 540
```

```
Lys Phe Leu Leu Met Leu Gln Ser Val Lys Arg Ala Phe Ala Ile Asp
545                 550                 555                 560

Ser Ser His Pro Trp Leu His Glu Cys Met Ile Arg Leu Phe His Ser
                565                 570                 575

Val Cys Glu Ser Lys Asp Leu Pro Glu Thr Val Arg Thr Val Leu Lys
                580                 585                 590

Gln Glu Met Asn Arg Leu Phe Gly Ala Thr Asn Pro Lys Asn Phe Asn
            595                 600                 605

Glu Thr Phe Leu Lys Arg Asn Ser Asp Ser Leu Pro His Arg Leu Ser
        610                 615                 620

Ala Ala Lys Met Val Tyr Tyr Leu Asp Ser Ser Gln Lys Arg Ala
625                 630                 635                 640

Ile Glu Leu Ala Thr Thr Leu Asp Gly Ser Leu Thr Asn Arg Asn Leu
                645                 650                 655

Gln Thr Cys Met Glu Val Leu Glu Ala Leu Cys Asp Gly Ser Leu Arg
            660                 665                 670

Asp Cys Lys Glu Ala Ala Glu Ala Tyr Arg Ala Ser Cys His Lys Leu
        675                 680                 685

Phe Pro Tyr Ala Leu Ala Phe Met Pro Pro Gly Tyr Glu Glu Asp Met
690                 695                 700

Lys Ile Thr Val Asn Gly Asp Ser Ser Ala Glu Thr Glu Glu Leu Ala
705                 710                 715                 720

Asn Glu Ile

<210> SEQ ID NO 4
<211> LENGTH: 710
<212> TYPE: PRT
<213> ORGANISM: Homo sapiens

<400> SEQUENCE: 4

Met Leu Tyr His Leu Leu Glu Asp Tyr Glu Met Ala Ala Lys Ile Leu
1               5                   10                  15

Glu Glu Phe Arg Lys Thr Gln Gln Thr Ser Pro Asp Lys Val Asp Tyr
                20                  25                  30

Glu Tyr Ser Glu Leu Leu Leu Tyr Gln Asn Gln Val Leu Arg Glu Ala
            35                  40                  45

Gly Leu Tyr Arg Glu Ala Leu Glu His Leu Cys Thr Tyr Glu Lys Gln
        50                  55                  60

Ile Cys Asp Lys Leu Ala Val Glu Thr Lys Gly Glu Leu Leu Leu
65                  70                  75                  80

Gln Leu Cys Arg Leu Glu Asp Ala Ala Asp Val Tyr Arg Gly Leu Gln
                85                  90                  95

Glu Arg Asn Pro Glu Asn Trp Ala Tyr Tyr Lys Gly Leu Glu Lys Ala
            100                 105                 110

Leu Lys Pro Ala Asn Met Leu Glu Arg Leu Lys Ile Tyr Glu Glu Ala
        115                 120                 125

Trp Thr Lys Tyr Pro Arg Gly Leu Val Pro Arg Lys Leu Pro Leu Asn
    130                 135                 140

Phe Leu Ser Gly Glu Lys Phe Lys Glu Cys Leu Asp Arg Phe Leu Arg
145                 150                 155                 160

Met Asn Phe Ser Lys Gly Cys Pro Pro Val Phe Asn Thr Leu Arg Ser
                165                 170                 175

Leu Tyr Arg Asp Lys Glu Lys Val Ala Ile Val Glu Glu Leu Val Val
            180                 185                 190
```

-continued

```
Gly Tyr Glu Thr Ser Leu Lys Ser Cys Arg Leu Phe Asn Pro Asn Asp
            195                 200                 205

Asp Gly Lys Glu Glu Pro Pro Thr Thr Leu Leu Trp Val Gln Tyr Tyr
            210                 215                 220

Leu Ala Gln His Tyr Asp Lys Ile Gly Gln Pro Ser Ile Ala Leu Glu
225                 230                 235                 240

Tyr Ile Asn Thr Ala Ile Glu Ser Thr Pro Thr Leu Ile Glu Leu Phe
                245                 250                 255

Leu Val Lys Ala Lys Ile Tyr Lys His Ala Gly Asn Ile Lys Glu Ala
            260                 265                 270

Ala Arg Trp Met Asp Glu Ala Gln Ala Leu Asp Thr Ala Asp Arg Phe
            275                 280                 285

Ile Asn Ser Lys Cys Ala Lys Tyr Met Leu Lys Ala Asn Leu Ile Lys
            290                 295                 300

Glu Ala Glu Glu Met Cys Ser Lys Phe Thr Arg Glu Gly Thr Ser Ala
305                 310                 315                 320

Val Glu Asn Leu Asn Glu Met Gln Cys Met Trp Phe Gln Thr Glu Cys
                325                 330                 335

Ala Gln Ala Tyr Lys Ala Met Asn Lys Phe Gly Glu Ala Leu Lys Lys
            340                 345                 350

Cys His Glu Ile Glu Arg His Phe Ile Glu Ile Thr Asp Asp Gln Phe
            355                 360                 365

Asp Phe His Thr Tyr Cys Met Arg Lys Ile Thr Leu Arg Ser Tyr Val
            370                 375                 380

Asp Leu Leu Lys Leu Glu Asp Val Leu Arg Gln His Pro Phe Tyr Phe
385                 390                 395                 400

Lys Ala Ala Arg Ile Ala Ile Glu Ile Tyr Leu Lys Leu His Asp Asn
                405                 410                 415

Pro Leu Thr Asp Glu Asn Lys Glu His Glu Ala Asp Thr Ala Asn Met
            420                 425                 430

Ser Asp Lys Glu Leu Lys Lys Leu Arg Asn Lys Gln Arg Arg Ala Gln
            435                 440                 445

Lys Lys Ala Gln Ile Glu Glu Lys Lys Asn Ala Glu Lys Glu Lys
            450                 455                 460

Pro Gln Arg Asn Pro Lys Lys Lys Asp Asp Asp Glu Glu Ile
465                 470                 475                 480

Gly Gly Pro Lys Glu Glu Leu Ile Pro Glu Lys Leu Ala Lys Val Glu
                485                 490                 495

Thr Pro Leu Glu Glu Ala Ile Lys Phe Leu Thr Pro Leu Lys Asn Leu
            500                 505                 510

Val Lys Asn Lys Ile Glu Thr His Leu Phe Ala Phe Glu Ile Tyr Phe
            515                 520                 525

Arg Lys Glu Lys Phe Leu Leu Met Leu Gln Ser Val Lys Arg Ala Phe
            530                 535                 540

Ala Ile Asp Ser Ser His Pro Trp Leu His Glu Cys Met Ile Arg Leu
545                 550                 555                 560

Phe His Ser Val Cys Glu Ser Lys Asp Leu Pro Glu Thr Val Arg Thr
                565                 570                 575

Val Leu Lys Gln Glu Met Asn Arg Leu Phe Gly Ala Thr Asn Pro Lys
            580                 585                 590

Asn Phe Asn Glu Thr Phe Leu Lys Arg Asn Ser Asp Ser Leu Pro His
            595                 600                 605
```

-continued

```
Arg Leu Ser Ala Ala Lys Met Val Tyr Tyr Leu Asp Ser Ser Gln
    610                 615                 620

Lys Arg Ala Ile Glu Leu Ala Thr Thr Leu Asp Gly Ser Leu Thr Asn
625                 630                 635                 640

Arg Asn Leu Gln Thr Cys Met Glu Val Leu Glu Ala Leu Cys Asp Gly
                    645                 650                 655

Ser Leu Arg Asp Cys Lys Glu Ala Ala Glu Ala Tyr Arg Ala Ser Cys
                660                 665                 670

His Lys Leu Phe Pro Tyr Ala Leu Ala Phe Met Pro Pro Gly Tyr Glu
            675                 680                 685

Glu Asp Met Lys Ile Thr Val Asn Gly Asp Ser Ser Ala Glu Thr Glu
        690                 695                 700

Glu Leu Ala Asn Glu Ile
705                 710

<210> SEQ ID NO 5
<211> LENGTH: 700
<212> TYPE: PRT
<213> ORGANISM: Homo sapiens

<400> SEQUENCE: 5

Met Ala Ala Lys Ile Leu Glu Glu Phe Arg Lys Thr Gln Gln Thr Ser
1               5                   10                  15

Pro Asp Lys Val Asp Tyr Glu Tyr Ser Glu Leu Leu Leu Tyr Gln Asn
                20                  25                  30

Gln Val Leu Arg Glu Ala Gly Leu Tyr Arg Glu Ala Leu Glu His Leu
            35                  40                  45

Cys Thr Tyr Glu Lys Gln Ile Cys Asp Lys Leu Ala Val Glu Glu Thr
    50                  55                  60

Lys Gly Glu Leu Leu Gln Leu Cys Arg Leu Glu Asp Ala Ala Asp
65                  70                  75                  80

Val Tyr Arg Gly Leu Gln Glu Arg Asn Pro Glu Asn Trp Ala Tyr Tyr
                85                  90                  95

Lys Gly Leu Glu Lys Ala Leu Lys Pro Ala Asn Met Leu Glu Arg Leu
            100                 105                 110

Lys Ile Tyr Glu Glu Ala Trp Thr Lys Tyr Pro Arg Gly Leu Val Pro
        115                 120                 125

Arg Lys Leu Pro Leu Asn Phe Leu Ser Gly Glu Lys Phe Lys Glu Cys
130                 135                 140

Leu Asp Arg Phe Leu Arg Met Asn Phe Ser Lys Gly Cys Pro Pro Val
145                 150                 155                 160

Phe Asn Thr Leu Arg Ser Leu Tyr Arg Asp Lys Glu Lys Val Ala Ile
                165                 170                 175

Val Glu Glu Leu Val Val Gly Tyr Glu Thr Ser Leu Lys Ser Cys Arg
            180                 185                 190

Leu Phe Asn Pro Asn Asp Asp Gly Lys Glu Glu Pro Pro Thr Thr Leu
        195                 200                 205

Leu Trp Val Gln Tyr Tyr Leu Ala Gln His Tyr Asp Lys Ile Gly Gln
    210                 215                 220

Pro Ser Ile Ala Leu Glu Tyr Ile Asn Thr Ala Ile Glu Ser Thr Pro
225                 230                 235                 240

Thr Leu Ile Glu Leu Phe Leu Val Lys Ala Lys Ile Tyr Lys His Ala
                245                 250                 255

Gly Asn Ile Lys Glu Ala Ala Arg Trp Met Asp Glu Ala Gln Ala Leu
            260                 265                 270
```

```
Asp Thr Ala Asp Arg Phe Ile Asn Ser Lys Cys Ala Lys Tyr Met Leu
        275                 280                 285

Lys Ala Asn Leu Ile Lys Glu Ala Glu Glu Met Cys Ser Lys Phe Thr
        290                 295                 300

Arg Glu Gly Thr Ser Ala Val Glu Asn Leu Asn Glu Met Gln Cys Met
305                 310                 315                 320

Trp Phe Gln Thr Glu Cys Ala Gln Ala Tyr Lys Ala Met Asn Lys Phe
                325                 330                 335

Gly Glu Ala Leu Lys Lys Cys His Glu Ile Glu Arg His Phe Ile Glu
                340                 345                 350

Ile Thr Asp Asp Gln Phe Asp Phe His Thr Tyr Cys Met Arg Lys Ile
                355                 360                 365

Thr Leu Arg Ser Tyr Val Asp Leu Leu Lys Leu Glu Asp Val Leu Arg
        370                 375                 380

Gln His Pro Phe Tyr Phe Lys Ala Ala Arg Ile Ala Ile Glu Ile Tyr
385                 390                 395                 400

Leu Lys Leu His Asp Asn Pro Leu Thr Asp Glu Asn Lys Glu His Glu
                405                 410                 415

Ala Asp Thr Ala Asn Met Ser Asp Lys Glu Leu Lys Lys Leu Arg Asn
                420                 425                 430

Lys Gln Arg Arg Ala Gln Lys Lys Ala Gln Ile Glu Glu Glu Lys Lys
        435                 440                 445

Asn Ala Glu Lys Glu Lys Pro Gln Arg Asn Pro Lys Lys Lys Lys Asp
        450                 455                 460

Asp Asp Asp Glu Glu Ile Gly Gly Pro Lys Glu Glu Leu Ile Pro Glu
465                 470                 475                 480

Lys Leu Ala Lys Val Glu Thr Pro Leu Glu Glu Ala Ile Lys Phe Leu
                485                 490                 495

Thr Pro Leu Lys Asn Leu Val Lys Asn Lys Ile Glu Thr His Leu Phe
                500                 505                 510

Ala Phe Glu Ile Tyr Phe Arg Lys Glu Lys Phe Leu Leu Met Leu Gln
        515                 520                 525

Ser Val Lys Arg Ala Phe Ala Ile Asp Ser Ser His Pro Trp Leu His
        530                 535                 540

Glu Cys Met Ile Arg Leu Phe His Ser Val Cys Glu Ser Lys Asp Leu
545                 550                 555                 560

Pro Glu Thr Val Arg Thr Val Leu Lys Gln Glu Met Asn Arg Leu Phe
                565                 570                 575

Gly Ala Thr Asn Pro Lys Asn Phe Asn Glu Thr Phe Leu Lys Arg Asn
                580                 585                 590

Ser Asp Ser Leu Pro His Arg Leu Ser Ala Ala Lys Met Val Tyr Tyr
        595                 600                 605

Leu Asp Ser Ser Ser Gln Lys Arg Ala Ile Glu Leu Ala Thr Thr Leu
        610                 615                 620

Asp Gly Ser Leu Thr Asn Arg Asn Leu Gln Thr Cys Met Glu Val Leu
625                 630                 635                 640

Glu Ala Leu Cys Asp Gly Ser Leu Arg Asp Cys Lys Glu Ala Ala Glu
                645                 650                 655

Ala Tyr Arg Ala Ser Cys His Lys Leu Phe Pro Tyr Ala Leu Ala Phe
                660                 665                 670
```

| Met | Pro | Pro | Gly | Tyr | Glu | Glu | Asp | Met | Lys | Ile | Thr | Val | Asn | Gly | Asp |
|---|---|---|---|---|---|---|---|---|---|---|---|---|---|---|---|
| | | | | 675 | | | | 680 | | | | 685 | | | |

| Ser | Ser | Ala | Glu | Thr | Glu | Glu | Leu | Ala | Asn | Glu | Ile |
|---|---|---|---|---|---|---|---|---|---|---|---|
| | 690 | | | | 695 | | | | 700 | | |

<210> SEQ ID NO 6
<211> LENGTH: 1779
<212> TYPE: DNA
<213> ORGANISM: Homo sapiens

<400> SEQUENCE: 6

```
atgttagaac ggctaaaaat atatgaggaa gcctggacta ataccccag gggactcgtg      60
ccaagaaagc tgcccttaaa cttttatct ggagagaagt ttaaggagtg tttggatagg     120
ttcctaagga tgaatttcag caagggctgt ccacctgtct tcaataccttt gaggtcttta    180
tacagagata aagagaaggt ggcaatcgta aagaactag tagttggtta tgaaacttct     240
ctaaaaagtt gtcgcctatt taaccccaat gatgatggaa aggaggaacc tccaaccaca    300
ttactttggg tccagtacta tttggcacag cattatgata aaattggtca gccatccatt    360
gctctggaat acataaatac tgcaattgaa agtacaccaa cattgataga actctttctt    420
gtaaaagcta aatctataa gcatgctggg aatattaaag aagctgccag gtggatggat    480
gaagcccagg ccctggacac agcagacaga tttattaatt ccaagtgtgc aaaatacatg    540
ttaaaagcca acctgattaa agaggctgaa gaaatgtgtt ccaagtttac gagggaagga    600
acttcagcgg tagagaacct gaatgaaatg cagtgtatgt ggttccagac agagtgtgct    660
caggcataca aagcaatgaa caaatttggt gaagcactta agaaatgtca tgaaattgag    720
agacatttta tagaaatcac cgatgaccag tttgactttc atacatactg tatgaggaag    780
atcaccctta gatcatatgt ggacttatta aaactagaag atgtacttcg acagcatcca    840
ttttacttca aagcagcgag aattgctatt gagatctatt tgaagcttca tgacaaccct    900
ctgacagatg agaacaaaga cacgaggct gatacagcaa acatgtctga caaagagcta    960
aagaaactgc gtaataaaca aagaagagct caaaagaaag cccagattga agaagagaaa   1020
aaaaatgccg aaaaagaaa gccgcaacgg aatccgaaaa agaaaaagga tgatgatgac   1080
gaagaaattg gaggccccaa agaagagctt atccctgaga aactggccaa ggttgaaact   1140
ccattggaag aagctattaa gtttttaaca ccattgaaga acttggtgaa gaacaagata   1200
gaaactcatc ttttgccttt tgagatctac tttaggaaag aaagtttct tttgatgcta   1260
caatcagtaa gcggggcatt tgctattgat tctagtcatc cctggcttca tgagtgcatg   1320
attcgactct tcattctgt gtgtgaaagt aaagacttac ccgaaacagt tagaacagta   1380
ttaaaacaag aaatgaatcg tcttttttgga gcaacaaatc caagaatttt taatgaaacc   1440
tttctgaaaa ggaattctga ttcattgcca catagattat cagctgccaa aatggtatat   1500
tatttagatt cttctagtca aaaacgagca atagagctgg cgacaacact tgatggatcc   1560
ctcaccaaca gaaaccttca gacttgcatg gaagtgttgg aagccttgtg tgatggtagc   1620
ctacgagact gtaaagaagc tgccgaagcc tacagagcaa gttgtcataa gcttttccct   1680
tatgctttgg ctttcatgcc tcctggatac gaagaggata tgaagatcac agtgaacgga   1740
gatagttctg cagaaacgga agaactggcc aatgaaatc                           1779
```